(12) United States Patent
Gong et al.

(10) Patent No.: US 9,783,499 B2
(45) Date of Patent: Oct. 10, 2017

(54) QUINOLINE DERIVATIVES AND THEIR APPLICATIONS

(71) Applicant: Shenyang Pharmaceutical University, Shenyang, Liaoning (CN)

(72) Inventors: Ping Gong, Shenyang (CN); Yanfang Zhao, Shenyang (CN); Yajing Liu, Shenyang (CN); Xin Zhai, Shenyang (CN)

(73) Assignee: Shenyang Pharmaceutical University, Shenyang (CN)

( * ) Notice: Subject to any disclaimer, the term of this patent is extended or adjusted under 35 U.S.C. 154(b) by 0 days.

(21) Appl. No.: 14/703,769

(22) Filed: May 4, 2015

(65) Prior Publication Data
US 2015/0307453 A1 Oct. 29, 2015

Related U.S. Application Data

(63) Continuation-in-part of application No. PCT/CN2013/085848, filed on Oct. 24, 2013.

(30) Foreign Application Priority Data

Nov. 5, 2012 (CN) .......................... 2012 1 0436831

(51) Int. Cl.
| C07D 215/233 | (2006.01) |
| C07D 215/36 | (2006.01) |
| C07D 215/42 | (2006.01) |
| C07D 401/12 | (2006.01) |

(52) U.S. Cl.
CPC ....... *C07D 215/233* (2013.01); *C07D 215/36* (2013.01); *C07D 215/42* (2013.01); *C07D 401/12* (2013.01)

(58) Field of Classification Search
CPC .................................................. C07D 215/233
See application file for complete search history.

(56) References Cited

FOREIGN PATENT DOCUMENTS

| JP | 2007-506777 A | 3/2007 |
| WO | 2005/030140 A2 | 4/2005 |
| WO | 2010/036831 A1 | 4/2010 |
| WO | 2011/018454 A1 | 2/2011 |

OTHER PUBLICATIONS

Qi, B., et al. "Discovery and optimization of novel 4-phenoxy-6,7-disubstituted quinolones possessing semicarbazones as c-Met kinase inhibitors." Bioorganic & Medicinal Chemistry. (Jun. 19, 2013), vol. 21, pp. 5246-5260.*
Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
Sierra, J.R., et al. "c-Met as a potential therapeutic target and biomarker in cancer." Therapeutic Advances in Medical Oncology. (2011), vol. 3 (S1), pp. S21-S35.*
Extended European Search Report, dated Apr. 15, 2016, for European Application No. EP 13850445.1-1462 / 2915806, 6 pages.
Translation of Japanese Office Action, mailed Jun. 21, 2016, for Japanese Application No. 2015-540034, 4 pages.

* cited by examiner

*Primary Examiner* — Noble Jarrell
*Assistant Examiner* — John S Kenyon
(74) *Attorney, Agent, or Firm* — Seed Intellectual Property Law Group; Hai Han

(57) ABSTRACT

The invention relates to a series of quinoline derivatives of general formula I, pharmaceutically acceptable salts, hydrates, solvates or prodrugs. Thereof M, $R_1$, $R_2$, X, Y and n are defined as claims. And the compounds of general formula I show potent inhibitory activity against c-Met kinase. The present invention further relates to the uses of the compounds, pharmaceutically acceptable salts and hydrates for the preparation of medicaments for the treatment and/or prevention of diseases caused by abnormal expression of c-Met kinase, especially for treatment and/or prevention of cancer.

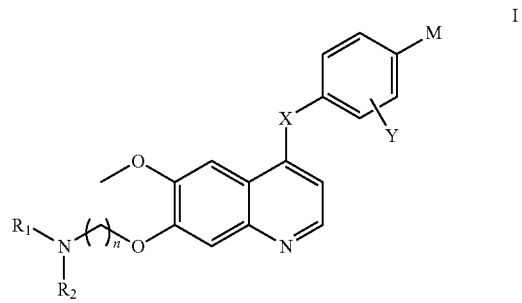

14 Claims, No Drawings

QUINOLINE DERIVATIVES AND THEIR APPLICATIONS

CROSS-REFERENCE TO RELATED APPLICATIONS

This application is a Continuation-in-Part application of International Patent Application No. PCT/CN2013/085848, filed Oct. 24, 2013, which claims priority to Chinese Patent Application No. 201210436831.4, filed Nov. 5, 2012, which applications are incorporated herein by reference in their entities.

FIELDS OF THE INVENTION

The invention relates to a new series of quinoline derivatives, their pharmaceutically acceptable salts, hydrates, solvates or prodrugs, methods for their preparation and pharmaceutical compositions containing these compounds. The invention also relates to the uses of these compounds, and their pharmaceutically acceptable salts, hydrates, solvates or prodrugs for the preparation of medicaments for the treatment and/or prevention of diseases caused by abnormal expression of c-Met kinase, especially for treatment and/or prevention of cancer.

BACKGROUND OF THE INVENTION

Cancer is a serious hazard to human life and health. With the changes of external factors such as environmental pollution, the number of cancer cases is rising year by year. Therefore, the study on the cancer mechanisms and the treatment methods of cancer is becoming more and more extensive.

In recent years, with the rapid development of tumor biology and related disciplines, some basic processes of cell carcinogenesis are gradually established, such as signal transduction in malignant tumor cell and cell apoptosis induction. The development of antitumor drugs has been gradually changed from interfering cell growth cycle to attacking the related enzymes of tumor cells, such as the epidermal growth factor and vascular endothelial growth factor, which makes the treatment of tumor change from the cellular level to the molecular level and produce many molecular-targeted drugs. On the basis of differences between normal cells and tumor cells, the new tumor target drugs can selectively act on tumor cell specific kinase of proliferation differentiation and have the advantages of high efficiency, low toxicity and strong specificity. So the research of kinase-targeted drugs has become the important direction.

Among the kinases as drug targets, protein kinases are the most deeply developed ones. The mutations and rearrangements of protein kinases lead to preventions or disorders in the process of signal transduction as first, and the cell disorder of growth, differentiation and proliferation subsequently and multitude tumors eventually.

Protein kinases (PKs), including protein tyrosine kinase (PTK) and serine-threonine kinase (STK), catalyze the phosphorylation of hydroxyl group on tyrosine, serine and threonine residues through the transfer of the end of ATP phosphate. Through signal transduction pathways, these enzymes regulate cell growth, differentiation and proliferation. By combining with growth factor ligand, the growth factor receptor PTK turns into an activated form, which interacts with the protein on the inner surface of cell membrane. It leads to the phosphorylation of the residues on receptors and other protein tyrosines, and the formation of multiple cytoplasmic signaling molecule complexes, which affect cell reaction, such as division (proliferation), differentiation, growth, metabolism and so on.

Growth factor receptors with PTK activity are called receptor tyrosine kinases (RTKs), which includes a big family of transmembrane receptors with multiple biological activities. c-Met is one of the members of Ron subfamily of RTK family, which is the only known high affinity receptor of hepatocyte growth factor (HGF). Human c-Met gene is located on the 7th chromosome (7q31), about 110 kb, included 21 exons. The mature c-Met is a heterodimeric which is composed of $5.0 \times 10^4$ α- and $1.4 \times 10^5$ β-subunits. α-Subunit is located in the extracellular, and β-subunit includes extracellular region, transmembrane region and intracellular region. Extracellular regions of α- and β-subunits are combined with HGF and act as the ligand recognition site. Whereas, the intracellular region possesses tyrosine kinase activity, which is the interacting parts of many signaling molecules. HGF/c-Met signaling pathways exist widely in all kinds of cells and play an essential role of physiological regulation during many tissues and organs of growth and development. But the overexpression of HGF or c-Met in cells lead to the invasion and metastasis of tumor cells. (Israel Cañadas, Federico Rojo, Montserrat Arumí-Uría, et al. Clin Transl Oncol. 2010, 12: 253-260)

As a kind of oncogene, the overexpression or down regulation of c-Met lead to tumor growth and invasion. Therefore, the expression of c-Met is considered to play a role in the early stage of tumor cell growth and migration. Stimulated by ligand HGF, c-Met starts a variety of physiological processes containing cell proliferation, motility, differentiation, angiogenesis, wound healing, tissue regeneration, embryonic development. Therefore, c-Met plays an important role in the enhancement of tumor cell growth, the modulation tumor cell metastasis, the advancement tumor cell invasion and the angiogenesis of tumor. For this reason, c-Met becomes an important target for the development of anticancer drug (Xiangdong Liu, Robert C. Newton, Peggy A. Scherle. Trends in Molecular Medicine. 2009, 16(1): 37-45).

Foretinib (GSK1363089, XL880), an quinoline derivative, is an oral c-Met and VEGFR/KDR kinase inhibitor with $IC_{50}$ values of 0.4 and 0.8 nM to c-Met and KDR, respectively. It has entered phase II clinical trial (WO2010036831A1). Foretinib has shown significant inhibitory effects against a variety of human tumor cell lines (such as human lung cancer cells, human gastric cancer cells, etc.), with an $IC_{50}$ values of about 0.004 mg/mL.

FIG. 1

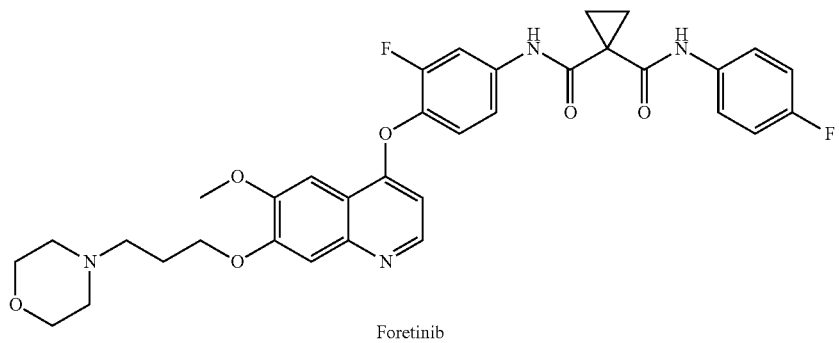

Foretinib

Basing on the reported literatures, the inventor designed and synthesized a new serial of quinoline derivatives, which possessed potent antitumor activity in vitro.

SUMMARY OF THE INVENTION

The invention relates to compounds of formula I, and their pharmaceutically acceptable salts, hydrates, solvates or prodrugs,

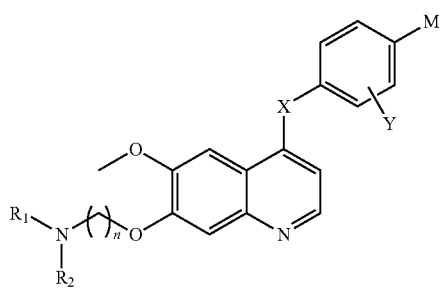

wherein,
X is O, S, NH or $NCH_3$;
Y can be 1-4 substituents optionally selected from halogen, trihalomethyl, methyl, cyano and nitro groups;
M is

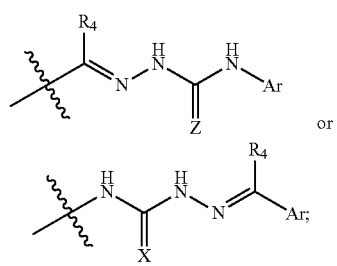

Z is O or S;
n is an integer between 1 and 6;
$R_1$ and $R_2$, which are same or different, are independently selected from hydrogen, ($C_1$-$C_{10}$) alkyl, ($C_3$-$C_7$) cycloalkyl, ($C_2$-$C_{10}$) alkenyl and ($C_2$-$C_{10}$) alkynyl, wherein $R_1$ and $R_2$ are optionally substituted with 1-3 same or different $R_3$;
Or $R_1$ and $R_2$ are covalently bonded together with the nitrogen atom to which they are attached to form 5- to 10-membered heterocyclic radical or 5- to 10-membered heteroaryl radical. Except the nitrogen atom to which $R_1$ and $R_2$ are attached, the said heterocyclic and heteroaryl radicals may contain 1 to 4 heteroatoms optionally selected from N, O and S. Except the nitrogen atom to which $R_1$ and $R_2$ are attached, the said heterocyclic radical may optionally contain 0 to 2 carbon-carbon double bonds or triple bonds. The said heterocyclic and heteroaryl radicals can be optionally substituted with 1 to 3 same or different $R_3$;
$R_3$ and $R_4$ are hydrogen or ($C_1$-$C_6$) alkyl;
Ar is ($C_6$-$C_{10}$) aryl or 5- to 10-membered heteroaryl radical. The said heteroaryl radical may contain 1 to 3 heteroatoms optionally selected from N, O and S. Ar can be optionally substituted with 1 to 3 same or different $R_5$;
$R_5$ is hydroxyl, halogen, nitro, amino, cyano, ($C_1$-$C_6$) alkyl, ($C_2$-$C_6$) alkenyl, ($C_2$-$C_6$) alkynyl, ($C_1$-$C_6$) alkoxyl, ($C_1$-$C_6$) alkyl or ($C_1$-$C_6$) alkoxyl which is optionally substituted with hydroxyl, amino or halogen, amino group substituted with 1 or 2 ($C_1$-$C_6$) alkyl groups, ($C_1$-$C_6$) alkylcarbonylamino, carboxyl group which can be free, salts, amidated or form ester group, ($C_1$-$C_6$) alkylsulfinyl, ($C_1$-$C_6$)alkylsulfonyl, ($C_1$-$C_6$) alkylacyl, carbamoyl, carbamoyl substituted with for 2 ($C_1$-$C_6$) alkyl, ($C_1$-$C_3$) alkylenedioxo, allyl.

The invention relates to compounds of the formula I, and their pharmaceutically acceptable salts, hydrates, solvates or prodrugs, wherein,
X is O, S, NH or $NCH_3$, wherein, O and S are preferred;
Y can be 1-2 substituents optionally selected from halogen, trihalomethyl, methyl, cyano and nitro groups;
M is

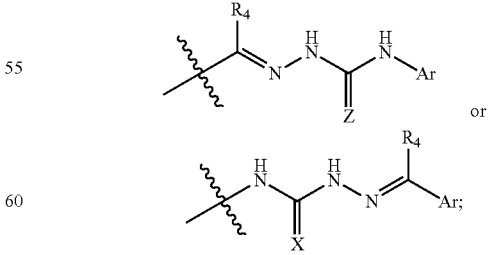

Z is O or S;
n is an integer between 1 and 4;
$R_1$ and $R_2$, which are same or different, are independently selected from hydrogen, ($C_1$-$C_6$)alkyl, ($C_3$-$C_5$)cycloalkyl, $(C_2-C_6)$alkenyl and $(C_2-C_6)$alkynyl, wherein $R_1$ and $R_2$ are optionally substituted with 1-3 same or different $R_3$;

Or $R_1$ and $R_2$ are covalently bonded together with the nitrogen atom to which they are attached to form 5- to 10-membered heterocyclic radical. Except the nitrogen atom to which $R_1$ and $R_2$ are attached, the said heterocyclic may contain 1 to 4 heteroatoms optionally selected from N, O and S. Except the nitrogen atom to which $R_1$ and $R_2$ are attached, the said heterocyclic radical may optionally contain 0 to 2 carbon-carbon double bonds or triple bonds. The said heterocyclic and heteroaryl radicals can be optionally substituted with 1 to 3 same or different $R_3$;

$R_3$ and $R_4$ are hydrogen or $(C_1-C_6)$ alkyl;

Ar is $(C_6-C_{10})$ aryl or 5- to 10-membered heteroaryl radical. The said heteroaryl radical may contain 1 to 3 heteroatoms optionally selected from N, O and S. Ar can be optionally substituted with 1 to 3 same or different $R_5$;

$R_5$ is hydroxyl, halogen, nitro, amino, cyano, $(C_1-C_6)$ alkyl, $(C_2-C_6)$ alkenyl, $(C_2-C_6)$ alkynyl, $(C_1-C_6)$ alkoxyl, $(C_1-C_6)$ alkyl or $(C_1-C_6)$ alkoxyl which is optionally substituted with hydroxyl, amino or halogen, amino group substituted with 1 or 2 $(C_1-C_6)$ alkyl groups, $(C_1-C_6)$ alkylcarbonylamino, carboxyl group which can be free, salts, amidated or form ester group, $(C_1-C_6)$ alkylsulfinyl, $(C_1-C_6)$ alkylsulfonyl, $(C_1-C_6)$ alkylacyl, carbamoyl, carbamoyl substituted with 1 or 2 $(C_1-C_6)$ alkyl, $(C_1-C_3)$ alkylenedioxo, allyl.

The invention relates to compounds of the formula II, and their pharmaceutically acceptable salts, hydrates, solvates or prodrugs, wherein,

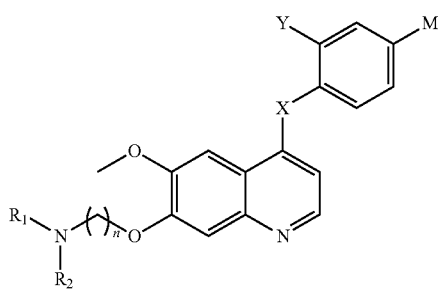

X is O;
Y is halogen, trihalomethyl, methyl, cyano or nitro groups;
Z is O or S;
n is 3 or 4;
$R_1$ and $R_2$, which are same or different, are independently selected from hydrogen, $(C_1-C_4)$ alkyl, $(C_3-C_5)$ cycloalkyl;

Or $R_1$ and $R_2$ are covalently bonded together with the nitrogen atom to which they are attached to form 5- or 6-membered heterocyclic radical. Except the nitrogen atom to which $R_1$ and $R_2$ are attached, the said heterocyclic radicals may contain 1 or 2 heteroatoms optionally selected from N, O and S. Except the nitrogen atom to which $R_1$ and $R_2$ are attached, the said heterocyclic radical may optionally contain 1 or 2 carbon-carbon double bonds or triple bonds. The said heterocyclic radical can be optionally substituted with 1 to 3 same or different $R_3$;

$R_3$ is $(C_1-C_4)$ alkyl;
$R_4$ is hydrogen or $(C_1-C_6)$ alkyl;
Ar is $(C_6-C_{10})$ aryl or 5- to 10-membered heteroaryl radical. Wherein the said heteroaryl radical may contain 1 to 3 heteroatoms optionally selected from N, O and S. And Ar can be optionally substituted with 1 to 3 same or different $R_5$;
$R_5$ is hydroxyl, halogen, nitro, amino, cyano, $(C_1-C_6)$ alkyl, $(C_2-C_6)$alkenyl, $(C_2-C_6)$alkynyl, $(C_1-C_6)$alkoxyl, $(C_1-C_6)$alkyl or $(C_1-C_6)$alkoxyl which is optionally substituted with hydroxyl, amino or halogen, amino group substituted with 1 or 2 $(C_1-C_6)$alkyl groups, $(C_1-C_6)$alkylcarbonylamino, carboxyl group which can be free, salts, amidated or form ester group, $(C_1-C_6)$ alkylsulfinyl, $(C_1-C_6)$alkylsulfonyl, $(C_1-C_6)$ alkylacyl, carbamoyl, carbamoyl substituted with for 2 $(C_1-C_6)$ alkyl, $(C_1-C_3)$ alkylenedioxo, allyl.

The invention relates to compounds of the formula I, and their pharmaceutically acceptable salts, hydrates, solvates or prodrugs, wherein, X is O;
Y is F;
Z is O or S;
n is 3;
$R_1$ and $R_2$ are covalently bonded together with the nitrogen atom to which they are attached to form dimethylamino, diethylamino, piperidin-1-yl, morpholin-4-yl, 4-methylpiperazin-1-yl, piperazin-1-yl, 4-methylpiperidin-1-yl, pyrrolidin-1-yl, thiomorpholin-4-yl; Among them, piperidin-1-yl, morpholin-4-yl, 4-methylpiperazin-1-yl, 4-methylpiperidin-1-yl, pyrrolidin-1-yl are preferred;
$R_4$ is hydrogen, methyl or ethyl; hydrogen is preferred;
Ar is $(C_6-C_{10})$ aryl, 5- to 10-membered heteroaryl radical. Wherein, the said heteroaryl radical may contain 1 to 3 heteroatoms selected from N, O and S. Ar is preferably selected from phenyl, naphthyl, quinolyl, isoquinolyl, quinazolinyl, indolyl, pyridyl, furanyl, thienyl, pyrrolyl and pyrimidinyl; phenyl is more preferred. And Ar can be optionally substituted with 1 to 3 same or different $R_5$;
$R_5$ is hydroxyl, halogen, nitro, amino, cyano, $(C_1-C_6)$ alkyl, $(C_2-C_6)$alkenyl, $(C_2-C_6)$alkynyl, $(C_1-C_6)$alkoxyl, $(C_1-C_6)$alkyl or $(C_1-C_6)$alkoxyl which is optionally substituted with hydroxyl, amino or halogen, amino group substituted with 1 or 2 $(C_1-C_6)$alkyl groups, $(C_1-C_6)$alkylcarbonylamino, carboxyl group which can be free, salts, amidated or form ester group, $(C_1-C_6)$ alkylsulfinyl, $(C_1-C_6)$alkylsulfonyl, $(C_1-C_6)$ alkoxyl, $(C_1-C_6)$alkyl, $(C_1-C_6)$alkylacyl, carbamoyl, carbamoyl substituted with 1 or 2 $(C_1-C_6)$alkyl, $(C_1-C_3)$alkylenedioxo, allyl. $R_5$ is preferably selected from halogen, hydroxyl, nitro, cyano, trifluoromethyl, trifluoromethoxy, $(C_1-C_4)$alkyl, $(C_1-C_4)$ alkoxy, allyl, dimethylamino and methylsulfonyl.

Compounds of formula I in the invention, and their pharmaceutically acceptable salts, hydrates, solvates or prodrugs are preferably selected from the following compounds. But these compounds do not mean any limit to this invention.

(E)-$N^1$-(3-fluoro-4-(6-methoxy-7-(3-(pyrrolidin-1-yl)propoxy)quinoline-4-yloxy)phenyl)-$N^4$-(benzaldehyde)semicarbazone;

(E)-$N^1$-(3-fluoro-4-(6-methoxy-7-(3-(4-methylpiperidin-1-yl)propoxy)quinoline-4-yloxy)phenyl)-$N^4$-(benzaldehyde)semicarbazone;

(E)-$N^1$-(3-fluoro-4-(6-methoxy-7-(3-(morpholin-4-yl)propoxy)quinoline-4-yloxy)phenyl)-$N^4$-(benzaldehyde)semicarbazone;

(E)-$N^1$-(3-fluoro-4-(6-methoxy-7-(3-(4-methylpiperazin-1-yl)propoxy)quinoline-4-lyoxy)phenyl)-$N^4$-(benzaldehyde)semicarbazone;

(E)-$N^1$-(3-fluoro-4-(6-methoxy-7-(3-(piperidin-1-yl)propoxy)quinoline-4-yloxy)phenyl)-$N^4$-(benzaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(3-methoxybenzaldehyde)semicarbazone;

(E)-$N^1$-(3-fluoro-4-(6-methoxy-7-(3-(4-methylpiperidin-1-yl)propoxy)quinoline-4-yloxy)-phenyl)-$N^4$-(3-methoxybenzaldehyde)semicarbazone;

(E)-$N^1$-(3-fluoro-4-(6-methoxy-7-(3-(morpholin-4-yl)propoxy)quinoline-4-yloxy)phenyl)-$N^4$-(3-methoxybenzaldehyde)semicarbazone;

(E)-$N^1$-(3-fluoro-4-(6-methoxy-7-(3-(piperidin-1-yl)propoxy)quinoline-4-yloxy)phenyl)-$N^4$-(3-methoxybenzaldehyde)semicarbazone;

(E)-$N^1$-(3-fluoro-4-(6-methoxy-7-(3-(4-methylpiperidin-1-yl)propoxy)quinoline-4-lyoxy)phenyl)-$N^4$-(4-fluorobenzaldehyde)semicarbazone;

(E)-$N^1$-(3-fluoro-4-(6-methoxy-7-(3-(piperidin-1-yl)propoxy)quinoline-4-yloxy)phenyl)-$N^4$-(4-fluorobenzaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(2-chloro-4-fluorobenzaldehyde)semicarbazone;

(E)-$N^1$-(3-fluoro-4-(6-methoxy-7-(3-(4-methylpiperidin-1-yl)propoxy)quinoline-4-yloxy)phenyl)-$N^4$-(2-chloro-4-fluorobenzaldehyde)semicarbazone;

(E)-$N^1$-(3-fluoro-4-(6-methoxy-7-(3-(morpholin-4-yl)propoxy)quinoline-4-yloxy)phenyl)-$N^4$-(2-chloro-4-fluorobenzaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(2-nitrobenzaldehyde)semicarbazone;

(E)-$N^1$-(3-fluoro-4-(6-methoxy-7-(3-(4-methylpiperidin-1-yl)propoxy)quinoline-4-yloxy)phenyl)-$N^4$-(2-nitrobenzaldehyde)semicarbazone;

(E)-$N^1$-(3-fluoro-4-(6-methoxy-7-(3-(piperidin-1-yl)propoxy)quinoline-4-yloxy)phenyl)-$N^4$-(2-nitrobenzaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(2-hydroxyl-1-naphthaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(2,4-dichlorobenzaldehyde) semicarbazone;

(E)-$N^1$-(3-fluoro-4-(6-methoxy-7-(3-(morpholin-4-yl)propoxy)quinoline-4-yloxy)phenyl)-$N^4$-(2,4-dichlorobenzaldehyde)semicarbazone;

(E)-$N^1$-(3-fluoro-4-(6-methoxy-7-(3-(4-methylpiperidin-1-yl)propoxy)quinoline-4-yloxy)phenyl)-$N^4$-(2-hydroxy-1-naphthaldehyde)semicarbazone;

(E)-$N^1$-(3-fluoro-4-(6-methoxy-7-(3-(pyrrolidin-1-yl)propoxy)quinoline-4-lyoxy)phenyl)-$N^4$-(3,4-difluorobenzaldehyde)semicarbazone;

(E)-$N^1$-(3-fluoro-4-(6-methoxy-7-(3-(morpholin-4-yl)propoxy)quinoline-4-oxy)phenyl)-$N^4$-(3,4-difluorobenzaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(3-trifluoromethylbenzaldehyde)semicarbazone;

(E)-$N^1$-(3-fluoro-4-(6-methoxy-7-(3-(4-methylpiperidin-1-yl)propoxy)quinoline-4-yloxy)phenyl)-$N^4$-(2,4-difluorobenzaldehyde)semicarbazone;

(E)-$N^1$-(3-fluoro-4-(6-methoxy-7-(3-(morpholin-4-yl)propoxy)quinoline-4-yloxy)phenyl)-$N^4$-(3-trifluoromethylbenzaldehyde)semicarbazone;

(E)-$N^1$-(3-fluoro-4-(6-methoxy-7-(3-(morpholin-4-yl)propoxy)quinoline-4-yloxy)phenyl)-$N^4$-(3,5-dimethyl-4-hydroxybenzaldehyde)semicarbazone;

(E)-$N^1$-(3-fluoro-4-(6-methoxy-7-(3-(morpholin-4-yl)propoxy)quinoline-4-yloxy)phenyl)-$N^4$-(2-hydroxyl-1-naphthaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(3-allyl-2-hydroxybenzaldehyde)semicarbazone;

(E)-$N^1$-(3-fluoro-4-(6-methoxy-7-(3-(pyrrolidin-1-yl)propoxy)quinoline-4-yloxy)phenyl)-$N^4$-(3-allyl-2-hydroxybenzaldehyde)semicarbazone;

(E)-$N^1$-(3-fluoro-4-(6-methoxy-7-(3-(piperidin-1-yl)propoxy)quinoline-4-yloxy)phenyl)-$N^4$-(3,4-difluorobenzaldehyde)thiosemicarbazone;

(E)-$N^1$-(3-fluoro-4-(6-methoxy-7-(3-(pyrrolidin-1-yl)propoxy)quinoline-4-yloxy)phenyl)-$N^4$-(2-nitrobenzaldehyde)thiosemicarbazone;

(E)-$N^1$-(3-fluoro-4-(6-methoxy-7-(3-(morpholin-4-yl)propoxy)quinoline-4-yloxy)phenyl)-$N^4$-(2-nitrobenzaldehyde)thiosemicarbazone;

(E)-$N^1$-(3-fluoro-4-(6-methoxy-7-(3-(piperidin-1-yl)propoxy)quinoline-4-yloxy)phenyl)-$N^4$-(2-nitrobenzaldehyde)thiosemicarbazone;

(E)-$N^1$-(3-fluoro-4-(6-methoxy-7-(3-(morpholin-4-yl)propoxy)quinoline-4-yloxy)phenyl)-$N^4$-(3-allyl-2-hydroxybenzaldehyde)thiosemicarbazone;

(E)-$N^1$-(3-fluoro-4-(6-methoxy-7-(3-(pyrrolidin-1-yl)propoxy)quinoline-4-yloxy)phenyl)-$N^4$-(benzaldehyde)thiosemicarbazone;

(E)-$N^1$-(3-fluoro-4-(6-methoxy-7-(3-(4-methylpiperidin-1-yl)propoxy)quinoline-4-yloxy)phenyl)-$N^4$-(benzaldehyde)thiosemicarbazone;

(E)-$N^1$-(3-fluoro-4-(6-methoxy-7-(3-(morpholin-4-yl)propoxy)quinoline-4-yloxy)phenyl)-$N^4$-(benzaldehyde)thiosemicarbazone;

(E)-$N^1$-(3-fluoro-4-(6-methoxy-7-(3-(4-methyl-1-piperazinyl)propoxy)quinoline-4-yloxy)phenyl)-$N^4$-(benzaldehyde)thiosemicarbazone;

(E)-$N^1$-(3-fluoro-4-(6-methoxy-7-(3-(4-methyl-1-piperazinyl)propoxy)quinoline-4-yloxy)phenyl)-$N^4$-(2,4-dichlorobenzaldehyde)thiosemicarbazone;

(E)-$N^1$-(3-fluoro-4-(6-methoxy-7-(3-(piperidin-1-yl)propoxy)quinoline-4-yloxy)phenyl)-$N^4$-(2,4-dichlorobenzaldehyde)thiosemicarbazone;

(E)-$N^1$-(3-fluoro-4-(6-methoxy-7-(3-(4-methyl-1-piperazinyl)propoxy)quinoline-4-yloxy)phenyl)-$N^4$-(2-chloro-4-fluorobenzaldehyde)thiosemicarbazone;

(E)-$N^1$-(3-fluoro-4-(6-methoxy-7-(3-(piperidin-1-yl)propoxy)quinoline-4-yloxy)phenyl)-$N^4$-(2-chloro-4-fluorobenzaldehyde)thiosemicarbazone;

(E)-$N^1$-(3-fluoro-4-(6-methoxy-7-(3-(pyrrolidin-1-yl)propoxy)quinoline-4-yloxy)phenyl)-$N^4$-(4-fluorobenzaldehyde)thiosemicarbazone;

(E)-$N^1$-(3-fluoro-4-(6-methoxy-7-(3-(morpholin-4-yl)propoxy)quinoline-4-yloxy)phenyl)-$N^4$-(4-fluorobenzaldehyde)thiosemicarbazone.

The invention preferentially relates to formula II and its pharmaceutically acceptable salts, hydrates, solvates or prodrugs:

(E)-N$^1$-(4-chloro-3-(trifluoromethyl)phenyl)-N$^4$-(3-fluoro-4-(6-methoxy-7-(3-(piperidin-1-yl)propoxy)quinoline-4-yloxy)benzaldehyde)semicarbazone;

(E)-N$^1$-(2-fluorophenyl)-N$^4$-(3-fluoro-4-(6-methoxy-7-(3-(piperidin-1-yl)propoxy)quinoline-4-yloxy)benzaldehyde)semicarbazone;

(E)-N$^1$-(3,5-dichlorophenyl)-N$^4$-(3-fluoro-4-(6-methoxy-7-(3-(piperidin-1-yl)propoxy)quinoline-4-yloxy)benzaldehyde)semicarbazone;

(E)-N$^1$-(3,5-dimethoxyphenyl)-N$^4$-(3-fluoro-4-(6-methoxy-7-(3-(piperidin-1-yl)propoxy)quinoline-4-yloxy)benzaldehyde)semicarbazone;

(E)-N$^1$-(3-fluoro-6-methylphenyl)-N$^4$-(-3-fluoro-4-(6-methoxy-7-(3-(piperidin-1-yl)propoxy)quinoline-4-yloxy)benzaldehyde)semicarbazone;

(E)-N$^1$-(4-chloro-3-(trifluoromethyl)phenyl)-N$^4$-(3-fluoro-4-(6-methoxy-7-(3-(4-methyl-1-piperazinyl)propoxy)quinoline-4-yloxy)benzaldehyde)semicarbazone;

(E)-N$^1$-phenyl-N$^4$-(3-fluoro-4-(6-methoxy-7-(3-(4-methyl-1-piperazinyl)propoxy)quinoline-4-yloxy benzaldehyde)semicarbazone;

(E)-N$^1$-(4-chlorophenyl)-N$^4$-(3-fluoro-4-(6-methoxy-7-(3-(4-methyl-1-piperazinyl)propoxy)quinoline-4-yloxy)benzaldehyde)semicarbazone;

(E)-N$^1$-(3-bromophenyl)-N$^4$-(3-fluoro-4-(6-methoxy-7-(3-(morpholin-4-yl)propoxy)quinoline-4-yloxy)benzaldehyde)semicarbazone;

(E)-N$^1$-phenyl-N$^4$-(3-fluoro-4-(6-methoxy-7-(3-(morpholin-4-yl)propoxy)quinoline-4-yloxy)benzaldehyde)semicarbazone;

(E)-N$^1$-(3,5-difluorophenyl)-N$^4$-(3-fluoro-4-(6-methoxy-7-(3-(morpholin-4-yl)propoxy)quinoline-4-yloxy)benzaldehyde)semicarbazone;

(E)-N$^1$-(3,5-dimethoxyphenyl)-N$^4$-(3-fluoro-4-(6-methoxy-7-(3-(morpholin-4-yl)propoxy)quinoline-4-oxy)benzaldehyde)semicarbazone;

(E)-N$^1$-phenyl-N$^4$-(3-fluoro-4-(6-methoxy-7-(3-(4-methylpiperidin-1-yl)propoxy)quinoline-4-yloxy)benzaldehyde)semicarbazone;

(E)-N$^1$-(3,5-dimethoxyphenyl)-N$^4$-(3-fluoro-4-(6-methoxy-7-(3-(4-methylpiperidin-1-yl)propoxy)quinoline-4-yloxy)benzaldehyde)semicarbazone;

(E)-N$^1$-(2-fluorophenyl)-N$^4$-(3-fluoro-4-(6-methoxy-7-(3-(4-methylpiperidin-1-yl)propoxy)quinoline-4-yloxy)benzaldehyde)semicarbazone;

(E)-N$^1$-(3,5-dichlorophenyl)-N$^4$-(3-fluoro-4-(6-methoxy-7-(3-(piperidin-1-yl)prop oxy)quinoline-4-yloxy)benzaldehyde)thiosemicarbazone;

(E)-N$^1$-(3,5-dimethoxyphenyl)-N$^4$-(4-(6-methoxy-7-(3-(piperidin-1-yl)propoxy)quinoline-4-yloxy)-3-fluorobenzaldehyde)thiosemicarbazone;

(E)-N$^1$-phenyl-N$^4$-(3-fluoro-4-(6-methoxy-7-(3-(4-methylpiperidin-1-yl)propoxy)quinoline-4-yloxy)benzaldehyde)thiosemicarbazone;

(E)-N$^1$-[4-chloro-3-(trifluoromethyl)phenyl]-N$^4$-(3-fluoro-4-(6-methoxy-7-(3-(4-methylpiperidin-1-yl)propoxy)quinoline-4-yloxy)benzaldehyde)thiosemicarbazone;

(E)-N$^1$-(3-bromophenyl)-N$^4$-(3-fluoro-4-(6-methoxy-7-(3-(morpholin-4-yl)propoxy)quinoline-4-yloxy)benzaldehyde)thiosemicarbazone;

(E)-N$^1$-(3,5-difluorophenyl)-N$^4$-(3-fluoro-4-(6-methoxy-7-(3-(morpholin-4-yl)propoxy)quinoline-4-yloxy)benzaldehyde)thiosemicarbazone;

(E)-N$^1$-phenyl-N$^4$-(3-fluoro-4-(6-methoxy-7-(3-(4-methyl-1-piperazinyl)propoxy)quinoline-4-yloxy)benzaldehyde)thiosemicarbazone;

(E)-N$^1$-(4-chlorophenyl)-N$^4$-(3-fluoro-4-(6-methoxy-7-(3-(4-methyl-1-piperazinyl)propoxy)quinoline-4-yloxy)benzaldehyde)thiosemicarbazone.

And that, according to some general methods involved in the field of the invention, suitable pharmaceutically acceptable salts are known to the quinoline derivatives defined as formula I. They include basic salts of inorganic and organic acids and the following acids are especially preferably selected: hydrochloric acid, hydrobromic acid, sulfuric acid, phosphoric acid, methane sulfonic acid, ethane sulfonic acid, para-toluene sulfonic acid, benzene sulfonic acid, naphthalene disulfonic acid, acetic acid, propanoic acid, lactic acid, trifluoroacetic acid, maleic acid, citric acid, fumaric acid, oxalic acid, tartaric acid and benzoic acid etc.

Furthermore, the present invention includes the pro-drugs of the compounds in the invention. According to the invention, the pro-drugs are the derivatives of the formula I, which have low biologically-activity and even have no biologically-activity in vitro, but which can convert to the corresponding biologically-active form in the physiological condition through metabolism, solvent decomposition and so on after administration.

In this invention, "halogen" refers to fluoro, chloro, bromo or iodo; "alkyl" refers to straight or branched chain alkyl; "alkylene" refers to straight or branched alkylene groups; the "cycloalkyl" refers to substituted or non-substituted cycloalkyl groups; the "aryl" refers to the substituted or no-substituted phenyl or naphthyl groups; the "heteroaryl" refers to the monocyclic or multicyclic systems containing one or more heteroatoms selected from N, O and S, which are aromatic, such as imidazolyl, pyridyl, pyrazolyl, (1,2,3)- and (1,2,4)-triazolyl, furanyl, thienyl, pyrrolyl, thiazolyl, benzothiazolyl, oxazolyl, isoxazolyl, quinolyl, isoquinolyl, benzimidazolyl and benzoxazolyl groups etc. "Saturated or partly saturated heterocylic group" refers to monocyclic or multicyclic systems containing one or more heteroatoms selected from N, O and S such as pyrrolidinyl, morpholinyl, piperazinyl, piperidinyl, pyrazolidinyl, imidazolidinyl and thiazolinyl.

We have found the compounds of present invention have an inhibitory activity on tumor cell growth. Hence, it can be used to prepare the drugs that can treat and/or prevent cancers, such as breast, lung, liver, kidney, colon, rectum, stomach, prostate, bladder, uterus, pancreas, bone marrow, testis, ovaries, lymph node, soft tissue, head and neck, thyroidea, esophagus cancer and leukemia, neuroblastoma and so on.

According to these tests against lung cancer cell H460, colon cancer cell HT-29, human gastric cancer cell MKN-45 and hepatoma cell line SMMC-7721, human breast cancer cell MDA-MB-231 and human glioblastoma cell U87MG, compounds in this invention showed remarkable inhibition on lung cancer cell, colon cancer cell, gastric cancer cell, hepatoma cell, breast cancer cell and glioblastoma cell lines etc. Therefore, the said compounds can be especially useful for the preparation of medicaments for treating and/or preventing of lung cancer, colon cancer, gastric cancer, breast cancer.

According to the test against c-Met, compounds of the present invention showed significant effects on inhibiting the activity of c-Met kinase, which is highly expressed in lung cancer cell, colon cancer cell, gastric cancer cell, breast cancer cell. As a result, these compounds are especially used to prepare the drugs that can treat and/or prevent lung cancer.

The active compounds, their pharmaceutically acceptable salts or solvates of the present invention may be used as a single anticancer medicament, or used in combination with anticancer drugs listed (Platinum drug, cisplatin; camptothecin drug irinotecan; *vinca* alkaloid drug, Navelbine; deoxycytidine celecoxib drug, gemcitabine; etoposide, paclitaxel, etc.). Such a combined therapy can be achieved by administrating respective therapeutic components simultaneously, subsequently or separately.

The following examples and preparation examples are provided to further illustrate and exemplify the compounds of the invention and preparation methods thereof. It shall not be understood that the following examples and preparation are intended to limit the scope of the invention in any way.

The following routes (Route 1, Route 2) illustrate the preparation of derivatives of general formula I of the present invention, wherein all starting materials can be prepared by the methods depicted in the schemes or the methods well known to ordinary technicians in the organic chemistry field, or are commercially available. All of the final derivatives in the present invention are prepared by the methods depicted in the schemes or similar methods, and these methods are well known to ordinary technicians in the organic chemistry field. All variable factors as involved in these schemes are defined as follows or in claims.

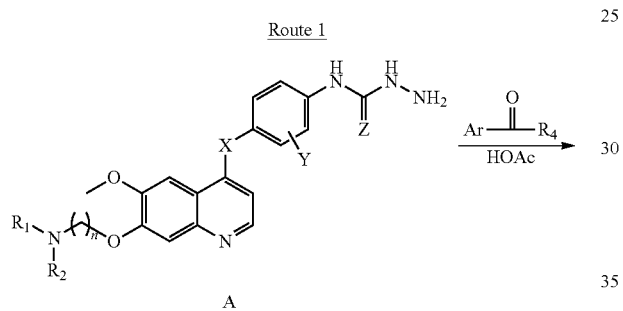

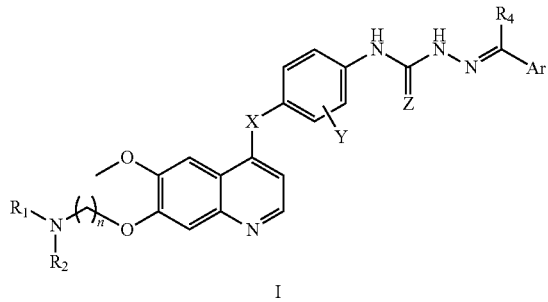

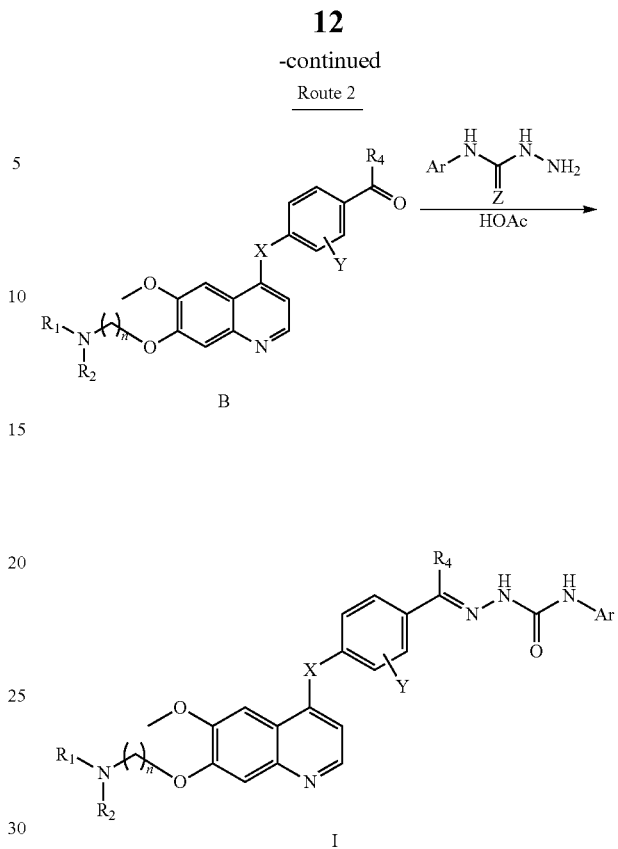

The derivatives of general formula I in this invention are obtained by condensation reaction of the corresponding intermediates A and aldehydes or intermediates B and (thio)semicarbazide in isopropanol at 80° C. for 5 h with catalytical amounts of acetic acid as illustrated in Route 1 and Route 2. Wherein, $R_1$, $R_2$, X, Y, Z and n are defined as claims in the invention.

When Z is O, the intermediates A-1 are prepared according to the method in Route 3:

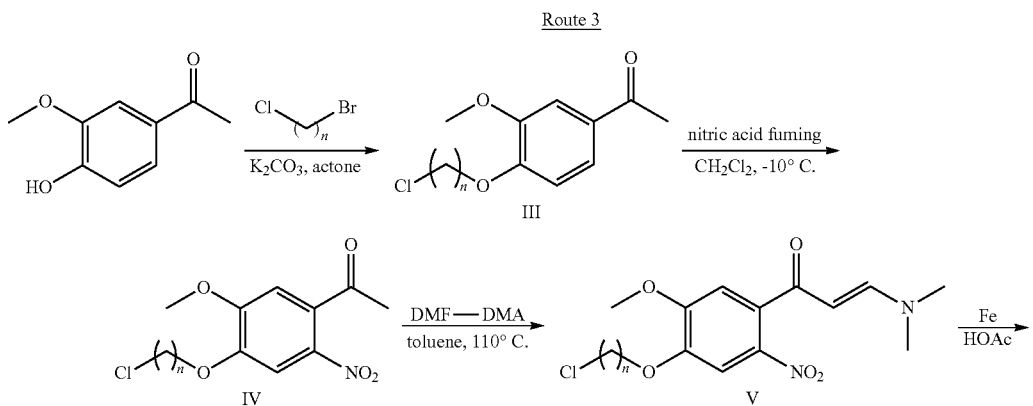

-continued
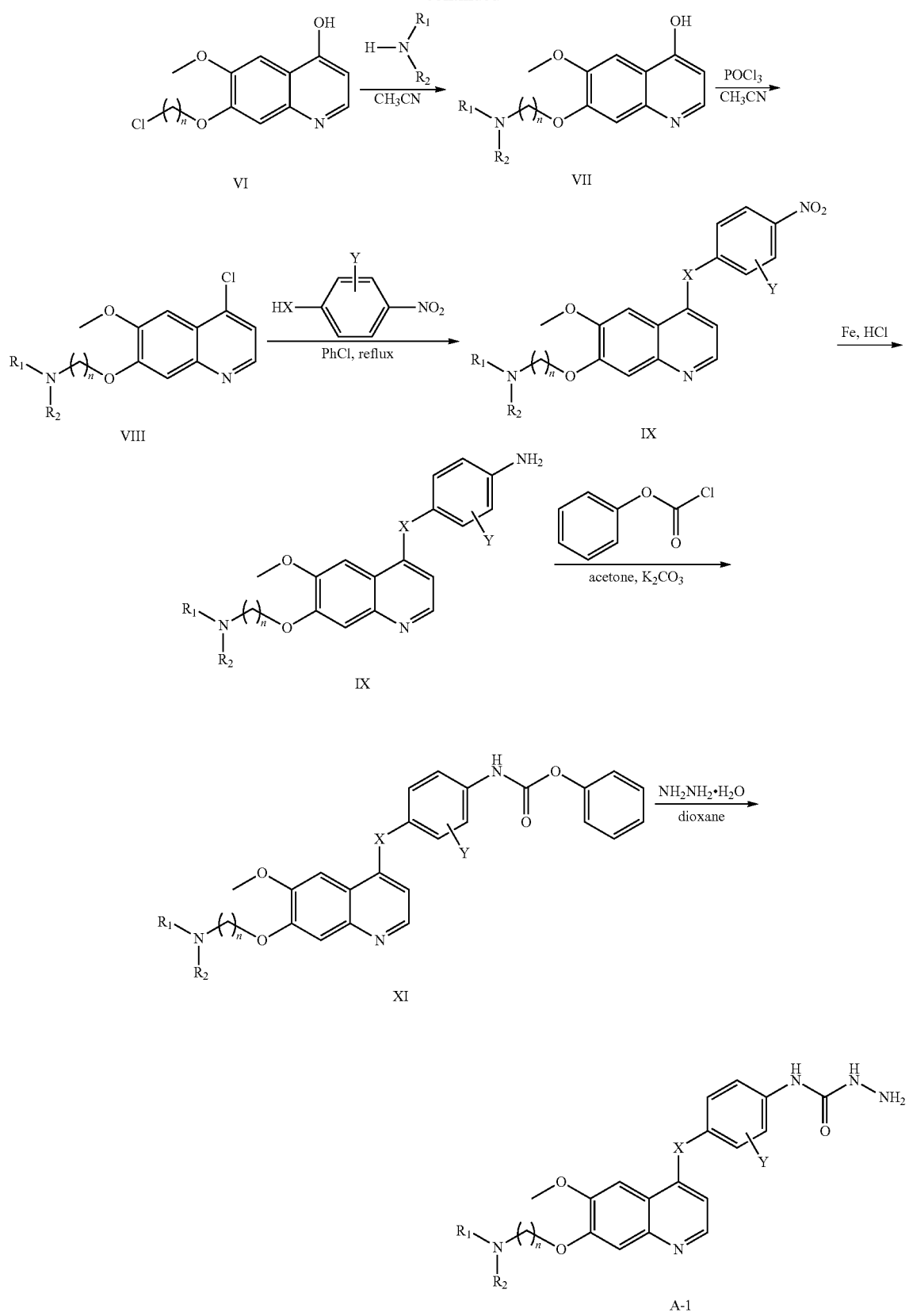

When Z is S, the intermediates A-2 are prepared according to the method in Route 4:

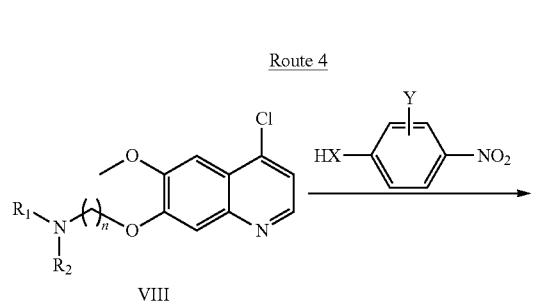

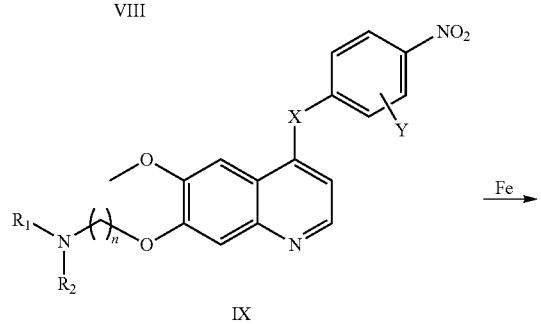

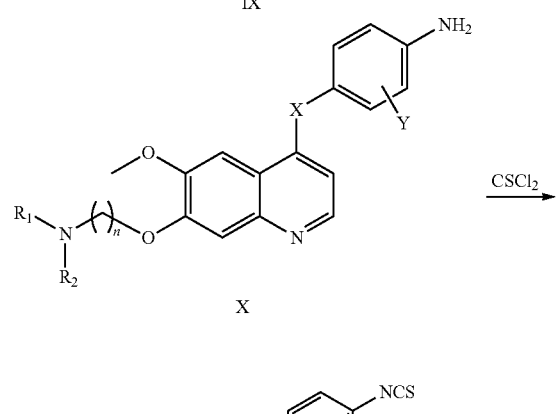

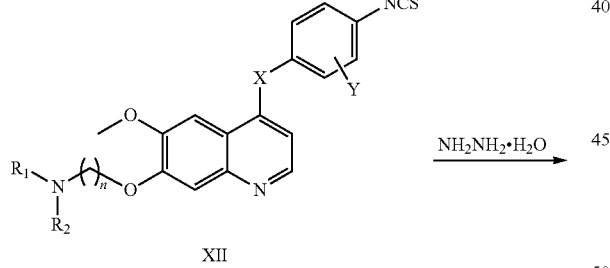

The intermediates B are prepared according to the method in Route 5:

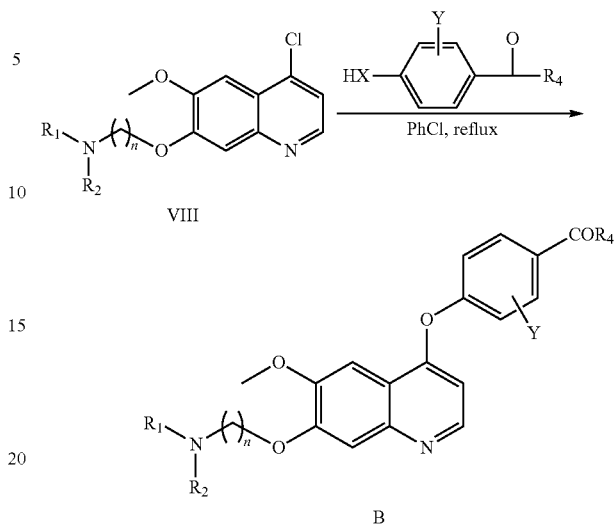

When Z is O, the intermediates W-2 are prepared according to the method in Route 6:

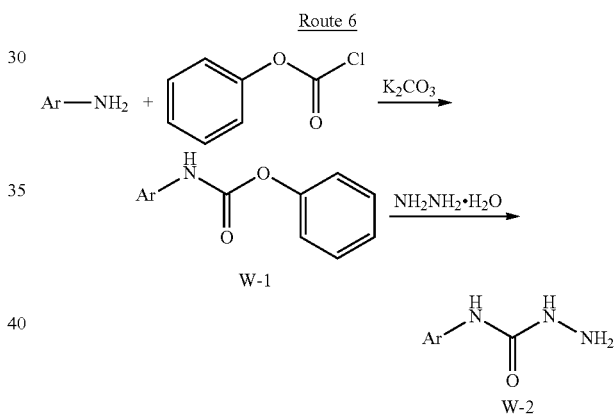

When Z is S, the intermediates W-4 are prepared according to the method in Route 7:

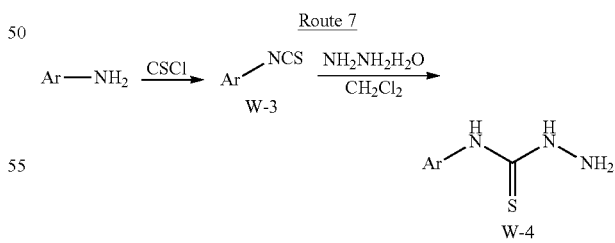

In those seven routes above, all substitutes including $R_1$, $R_2$, X, Y, Z and n of all intermediates are defined as claims in this invention.

EMBODIMENTS

The following examples aim to illustrate rather than limit the scope of the invention. The nuclear magnetic resonance hydrogen spectrum ($^1$H-NMR) of compounds in the invention was determined by Bruker ARX-300, and mass spectrum (MS) was determined by Agilent 1100 LC/MSD; all reagents were analytically pure or chemically pure.
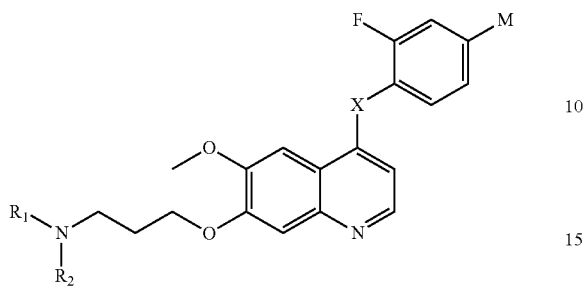
| Example | —NR$_1$R$_2$ | M |
|---|---|---|
| Example 1 |  |  |
| Example 2 | 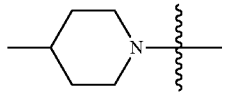 | 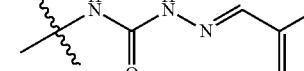 |
| Example 3 | 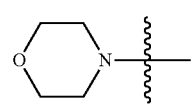 | 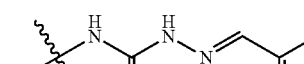 |
| Example 4 |  | 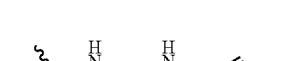 |
| Example 5 |  | 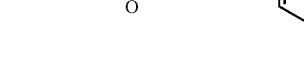 |
| Example 6 | 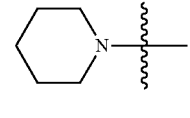 |  |
| Example 7 | 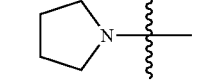 | 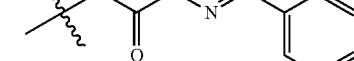 |
| Example 8 | 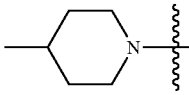 | 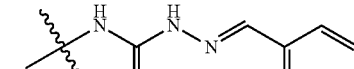 |

-continued

| Example | —NR₁R₂ | M |
|---|---|---|
| Example 9 | piperidinyl | semicarbazone of 3-methoxybenzaldehyde |
| Example 10 | 4-methylpiperidinyl | semicarbazone of 4-fluorobenzaldehyde |
| Example 11 | piperidinyl | semicarbazone of 4-fluorobenzaldehyde |
| Example 12 | pyrrolidinyl | semicarbazone of 2-chloro-4-fluorobenzaldehyde |
| Example 13 | 4-methylpiperidinyl | semicarbazone of 2-chloro-4-fluorobenzaldehyde |
| Example 14 | morpholinyl | semicarbazone of 2-chloro-4-fluorobenzaldehyde |
| Example 15 | pyrrolidinyl | semicarbazone of 2-nitrobenzaldehyde |
| Example 16 | 4-methylpiperidinyl | semicarbazone of 2-nitrobenzaldehyde |
| Example 17 | piperidinyl | semicarbazone of acetophenone |
| Example 18 | pyrrolidinyl | semicarbazone of 2-hydroxy-1-naphthaldehyde |

-continued

| Example | —NR₁R₂ | M |
|---|---|---|
| Example 19 | pyrrolidine | semicarbazone of 2,4-dichlorobenzaldehyde |
| Example 20 | morpholine | semicarbazone of 2,4-dichlorobenzaldehyde |
| Example 21 | 4-methylpiperidine | semicarbazone of 2-hydroxy-1-naphthaldehyde |
| Example 22 | pyrrolidine | semicarbazone of 3,4-difluorobenzaldehyde |
| Example 23 | morpholine | semicarbazone of 3,4-difluorobenzaldehyde |
| Example 24 | pyrrolidine | semicarbazone of 3-(trifluoromethyl)benzaldehyde |
| Example 25 | 4-methylpiperidine | semicarbazone of 2,4-difluorobenzaldehyde |
| Example 26 | morpholine | semicarbazone of 3-(trifluoromethyl)benzaldehyde |
| Example 27 | morpholine | semicarbazone of 4-hydroxy-3,5-dimethylbenzaldehyde |
| Example 28 | morpholine | semicarbazone of 2-hydroxy-1-naphthaldehyde |

-continued

| Example | —NR₁R₂ | M |
|---|---|---|
| Example 29 | pyrrolidinyl | semicarbazone of 2-hydroxy-3-allylbenzaldehyde |
| Example 30 | piperidinyl | semicarbazone of propiophenone |
| Example 31 | morpholinyl | thiosemicarbazone of 3,4-difluorobenzaldehyde |
| Example 32 | pyrrolidinyl | thiosemicarbazone of 2-nitrobenzaldehyde |
| Example 33 | morpholinyl | thiosemicarbazone of 2-nitrobenzaldehyde |
| Example 34 | piperidinyl | thiosemicarbazone of 2-nitrobenzaldehyde |
| Example 35 | morpholinyl | thiosemicarbazone of 2-hydroxy-3-allylbenzaldehyde |
| Example 36 | pyrrolidinyl | thiosemicarbazone of benzaldehyde |
| Example 37 | 4-methylpiperidinyl | thiosemicarbazone of benzaldehyde |
| Example 38 | morpholinyl | thiosemicarbazone of benzaldehyde |

-continued

| Example | —NR₁R₂ | M |
|---|---|---|
| Example 39 | N-methylpiperazinyl | thiosemicarbazone of benzaldehyde |
| Example 40 | N-methylpiperazinyl | thiosemicarbazone of 2,4-dichlorobenzaldehyde |
| Example 41 | piperidinyl | thiosemicarbazone of 2,4-dichlorobenzaldehyde |
| Example 42 | N-methylpiperazinyl | thiosemicarbazone of 2-chloro-4-fluorobenzaldehyde |
| Example 43 | piperidinyl | thiosemicarbazone of 2-chloro-4-fluorobenzaldehyde |
| Example 44 | pyrrolidinyl | thiosemicarbazone of 4-fluorobenzaldehyde |
| Example 45 | morpholinyl | thiosemicarbazone of 4-fluorobenzaldehyde |
| Example 46 | piperidinyl | semicarbazone with 4-chloro-3-(trifluoromethyl)phenyl |
| Example 47 | piperidinyl | semicarbazone with 2-fluorophenyl |
| Example 48 | piperidinyl | semicarbazone with 3,5-dichlorophenyl |

-continued

| Example | —NR₁R₂ | M |
|---|---|---|
| Example 49 | piperidinyl | semicarbazone-3,5-dimethoxyphenyl |
| Example 50 | piperidinyl | semicarbazone-2-methyl-5-fluorophenyl |
| Example 51 | 4-methylpiperazinyl | semicarbazone-3-trifluoromethyl-4-chlorophenyl |
| Example 52 | 4-methylpiperazinyl | semicarbazone-phenyl |
| Example 53 | 4-methylpiperazinyl | semicarbazone-4-chlorophenyl |
| Example 54 | morpholinyl | semicarbazone-3-bromophenyl |
| Example 55 | morpholinyl | semicarbazone-phenyl |
| Example 56 | morpholinyl | semicarbazone-3,5-difluorophenyl |
| Example 57 | morpholinyl | semicarbazone-3,5-dimethoxyphenyl |
| Example 58 | 4-methylpiperidinyl | semicarbazone-phenyl |

-continued

| Example | —NR₁R₂ | M |
|---|---|---|
| Example 59 | 4-methylpiperidin-1-yl | (E)-2-(1-methylethylidene)-N-(3,5-dimethoxyphenyl)hydrazinecarboxamide |
| Example 60 | 4-methylpiperidin-1-yl | (E)-N-(2-fluorophenyl)hydrazinecarboxamide |
| Example 61 | piperidin-1-yl | (E)-N-(3,5-dichlorophenyl)hydrazinecarbothioamide |
| Example 62 | piperidin-1-yl | (E)-N-(3,5-dimethoxyphenyl)hydrazinecarbothioamide |
| Example 63 | 4-methylpiperidin-1-yl | (E)-N-phenylhydrazinecarbothioamide |
| Example 64 | 4-methylpiperidin-1-yl | (E)-N-(4-chloro-3-(trifluoromethyl)phenyl)hydrazinecarbothioamide |
| Example 65 | morpholin-4-yl | (E)-N-(3-bromophenyl)hydrazinecarbothioamide |
| Example 66 | morpholin-4-yl | (E)-N-(3,5-difluorophenyl)hydrazinecarbothioamide |
| Example 67 | 4-methylpiperazin-1-yl | (E)-N-phenylhydrazinecarbothioamide |
| Example 68 | 4-methylpiperazin-1-yl | (E)-N-(4-chlorophenyl)hydrazinecarbothioamide |

Example 1

Step A: 1-(4-(3-Chloropropoxy)-3-methoxy)acetophenone (III)

1-(4-Hydroxy-3-methoxyphenyl)ethanone (600 g, 3.61 mol, Purchased from Zhejiang Dongdong Pharmaceutical Co., Ltd.) and anhydrous potassium carbonate (698 g, 5.055 mol) was added to 2500 mL of dry N,N-dimethylformamide. The mixture was stirred for 30 min at room temperature and then 1-bromo-3-chloropropane (795.9 g, 1.4 mol) was dropwise added while maintaining the temperature below 25° C. Then the resulted mixture was kept at 25° C. for 10 h. After completion of the reaction, the precipitate was filtered and the filter cake was washed by a small amount of N,N-dimethylformamide. The filtrate was poured into ice-water slowly with vigorous stirring. Then the resulted mixture was stirred for 30 min. The precipitate was filtered, washed with water, and dried to give 827.2 g as white solid. Yield: 93.8%.

Step B: 1-(4-(3-chloropropoxy)-5-methoxy-2-nitrophenyl)ethanone (N)

To a solution of intermediate III (200 g, 0.82 mol) in dichloromethane (1000 mL), fuming nitric acid (130 g, 2.06 mol) was added drop-wise at a rate to maintain the reaction temperature at −10~-20° C. Upon the completion of addition, the mixture was stirred for 2 h at −10~-20° C. After completion of the reaction, the reaction mixture was poured slowly into ice water, and the organic layer was separated and washed with saturated sodium bicarbonate solution until the aqueous layer became neutral, then dried with anhydrous sodium sulphate. The solution was evaporated to give 210.0 g yellow solid. Yield: 89.0%.

Step C: (E)-1-(4-(3-chloropropoxy)-5-methoxy-2-nitrophenyl)-3-(dimethylamino)prop-2-en-1-one (V)

To 1000 mL of toluene were added 0.695 mol (200 g) of intermediate N and the mixture was heated to 110° C. to make intermediate N completely dissolved. Then 3.476 mol (414.2 g) of N,N-dimethylformamide dimethyl acetal (DMF-DMA) was added, and the reaction was heated to reflux for 16 h. After completion of the reaction, the resulting precipitate from the cooled reaction (−10° C.) mixture was filtered to obtain the target compound as a yellow powder (180.0 g). Yield: 75.8%.

Step D: 7-(3-chloropropoxy)-6-methoxyquinolin-4(1H)-one (VI)

0.44 mol (150 g) of intermediate V was dissolved in 1200 mL of glacial acetic acid, and the mixture was heated to 40° C. After intermediate V was completely dissolved, 2.20 mol (123.1 g) ironpowder was added slowly, then the reaction mixture was heated to 80° C. with mechanical stirring for 2 h. After completion of the reaction, the reaction mixture was filtered immediately to remove iron powder. The filtrate was collected and cooled to precipitate solid, and then filtered to give yellow solid, which was dissolved in glacial acetic acid and recrystallized to give solid 79.0 g. Yield: 65.0%.

Step E: 6-methoxy-7-(3-(pyrrolidin-1-yl)propoxy)quinolin-4(1H)-one (VII)

To 620 mL of acetonitrile were added 0.232 mol (62 g) of intermediate VI, and 1.16 mol of pyrrolidine (82.46 g), then the reaction mixture was heated to reflux for 8 h. After completion of the reaction, most of the solvent was evaporated, the raffinate was put in cold trap to precipitated solid, then filtered and the filter cake was washed with ethyl acetate to give solid 66.7 g. Yield 95.3%.

Step F: 4-chloro-6-methoxy-7-(3-(pyrrolidin-1-yl)propoxy)quinolone (VIII)

To 315 mL of acetonitrile were added 0.198 mol (63.0 g) of intermediate VII, 315 ml of phosphorus oxychloride, then the reaction mixture was heated to 85° C. and refluxed for 6 h. After completion of the reaction, the mixture was evaporated to give gray viscous solid, which was poured into plenty of ice water, adjusted to pH 8 with 10% solution of potassium hydroxide, extracted with methylene dichloride (3×200 mL). The organic layer was collected and dried with anhydrous sodium sulfate, and evaporated in vacuo to give solid 58.1 g. Yield: 87.3%.

Step G: 4-(2-fluoro-4-nitrophenoxy)-6-methoxy-7-(3-(pyrrolidin-1-yl)propoxy)quinolone (IX)

To 250 mL of anhydrous chlorobenzene were added 0.234 mol (36.7 g) of 2-fluoro-4-nitrophenol. The reaction mixture was heated to 140° C. then added 0.2 mol (62.5 g) of intermediate (VIII). The resulted reaction mixture was kept at this temperature for 20 h. After completion of the reaction, the reaction mixture was evaporated in vacuo to give gray solid, which was dissolved with methylene dichloride and washed with saturated potassium carbonate solution. The organic layer was dried with sodium sulfate, evaporated and recrystallized with ethanol to give solid 49.3 g. Yield: 71.4%.

Step H: 3-fluoro-4-((6-methoxy-7-(3-(pyrrolidin-1-yl)propoxy)quinolin-4-yl)oxy)aniline (X)

To 1200 mL of 90% ethanol were added 1.1 mol (61.4 g) of ironpowder, 6 mL of hydrochloric acid, then the reaction mixture was heated to 80° C. with stirring and kept at this temperature for 15 min. After that, the reaction mixture was added portionwise 0.11 mol (48.4 g) intermediate IX, then refluxed for 2 h. After completion of the reaction, the reaction mixture was filtered with cooling. The filtrate was collected and evaporated to give yellow solid 43.2 g. Yield: 95.1%.

Step I: (3-Fluoro-4-(6-methoxy-7-(3-(pyrrolidin-1-yl)propoxy)quinolin-4-yloxy)phenyl)-4-(benzylidene)semicarbazide (XI)

To the mixture of intermediate X 39.5 g (0.09 mol) and anhydrous K$_2$CO$_3$ 24.8 g (0.18 mol) in dry acetone (500 mL), phenyl chloroformate 17.5 mL (0.14 mol) was added dropwise. After the addition was completed, the mixture was warmed to room temperature for another 3 h, and the solvent was evaporated under reduced pressure. The residue was dissolved in CH$_2$Cl$_2$ (500 mL), and washed with water (3×100 mL), dried over anhydrous Na$_2$SO$_4$, concentrated under reduced pressure to afford corresponding phenylcarbamates 45.1 g, Yield: 91.9%.

Step J: 3-fluoro-4-(6-methoxy-7-(3-(pyrrolidin-1-yl)propoxy)quinolin-4-yloxy)phenyl)semicarbazide (A-1)

A mixture of intermediate XI 45.1 g (0.08 mol) was dissolved in 1,4-dioxane (200 mL) and 80% hydrazine monohydrate (300 mL) was added and refluxed for 8 h with vigorous agitation. The solvent was evaporated under reduced pressure when white solid appeared. The resulting precipitate was filtered off to afford the title compound (17.8 g) as a yellow solid, yield: 46.1%.

Step K: (E)-$N^1$-(3-fluoro-4-(6-methoxy-7-(3-(pyrrolidin-1-yl)propoxy)quinolin-4-yloxy)phenyl)-$N^4$-(benzylidene)semicarbazide Example 1

To a solution of A-1 0.2 g (0.41 mmol) in isopropanol (2 mL), benzaldehydes and acetic acid (1 drop) were added, and the mixture was refluxed for 5 h. After cooling to room temperature, the resultant precipitate was filtered and washed with small amount of isopropanol to afford the title compound (0.16 g) as a white solid, yield: 63.6%.
ESI-MS [M+H] (m/z): 558.5; $^1$H-NMR (300 MHz, DMSO) δ10.92 (s, 1H), 9.23 (s, 1H), 8.49 (d, J=5.4 Hz, 1H), 7.99 (s, 1H), 7.90-7.97 (dd, $J_1$=13.5 Hz, $J_2$=2.4 Hz, 1H), 7.86-7.89 (m, 2H), 7.64-7.69 (m, 1H), 7.55 (s, 1H), 7.38-7.48 (m, 5H), 6.46 (d, J=5.1 Hz, 1H), 4.21 (t, J=6.3 Hz, 2H), 3.96 (s, 3H), 2.58 (t, J=6.9 Hz, 2H), 2.41-2.50 (m, 4H), 1.95-2.04 (m, 2H), 1.63-1.74 (m, 4H).
According to the methods in example 1, example 2-30 can be obtained by condensation reaction from varies substituted intermediates A-1 reacted with corresponding aldehydes.

Example 2

(E)-$N^1$-(3-fluoro-4-(6-methoxy-7-(3-(4-methylpiperidin-1-yl)propoxy)quinoline-4-yloxy)phenyl)-$N^4$-(benzaldehyde)semicarbazone ESI-MS [M+H] (m/z): 586.8; $^1$H-NMR (300 MHz, DMSO) δ10.91 (s, 1H), 9.22 (s, 1H), 8.47 (d, J=5.4 Hz, 1H), 7.97 (s, 1H), 7.90-7.95 (dd, $J_1$=13.5 Hz, $J_2$=2.1 Hz, 1H), 7.84-7.88 (m, 2H), 7.64-7.70 (m, 1H), 7.53 (s, 1H), 7.38-7.48 (m, 5H), 6.46 (d, J=5.1 Hz, 1H), 4.21 (t, J=6.3 Hz, 2H), 3.96 (s, 3H), 2.97 (br s, 2H), 2.53-2.67 (m, 2H), 1.92-2.14 (m, 4H), 1.58-1.69 (m, 2H), 1.39 (br s, 1H), 1.11-1.27 (m, 2H), 0.91 (d, J=6.6 Hz, 3H).

Example 3

(E)-$N^1$-(3-fluoro-4-(6-methoxy-7-(3-(morpholin-4-yl)propoxy)quinoline-4-yloxy)phenyl)-$N^4$-(benzaldehyde)semicarbazone ESI-MS [M+H] (m/z): 574.7; $^1$H-NMR (300 MHz, DMSO) δ10.93 (s, 1H), 9.23 (s, 1H), 8.48 (d, J=5.1 Hz, 1H), 8.00 (s, 1H), 7.91-7.96 (dd, $J_1$=16.5 Hz, $J_2$=2.4 Hz, 1H), 7.86-7.89 (m, 2H), 7.65-7.68 (m, 1H), 7.59 (s, 1H), 7.39-7.48 (m, 5H), 6.46 (d, J=5.1 Hz, 1H), 4.21 (t, J=6.3 Hz, 2H), 3.93 (s, 3H), 3.68 (m, 4H), 2.44-2.49 (m, 2H), 2.35-2.43 (br s, 4H), 1.94-2.03 (m, 2H).

Example 4

(E)-$N^1$-(3-fluoro-4-(6-methoxy-7-(3-(4-methylpiperazin-1-yl)propoxy)quinoline-4-lyoxy)phenyl)-$N^4$-(benzaldehyde)semicarbazone ESI-MS [M+H] (m/z): 587.6; $^1$H-NMR (300 MHz, DMSO) δ10.98 (s, 1H), 9.29 (s, 1H), 8.45 (d, J=5.1 Hz, 1H), 8.05 (s, 1H), 7.92-7.98 (dd, $J_1$=16.5 Hz, $J_2$=2.4 Hz, 1H), 7.86-7.89 (m, 2H), 7.64-7.70 (m, 1H), 7.62 (s, 1H), 7.41-7.49 (m, 5H), 6.47 (d, J=5.1 Hz, 1H), 4.29 (d, J=5.9 Hz, 2H), 3.98 (s, 3H), 3.38-3.47 (m, 10H), 2.85 (s, 3H), 2.39 (s, 2H).

Example 5

(E)-$N^1$-(3-fluoro-4-(6-methoxy-7-(3-(piperidin-1-yl)propoxy)quinoline-4-yloxy)phenyl)-$N^4$-(benzaldehyde)semicarbazone ESI-MS [M+H] (m/z): 571.6; $^1$H-NMR (300 MHz, DMSO) δ10.93 (s, 1H), 9.24 (s, 1H), 8.47 (d, J=5.1 Hz, 1H), 7.99 (s, 1H), 7.90-7.95 (dd, $J_1$=13.6 Hz, $J_2$=2.4 Hz, 1H), 7.86-7.88 (m, 2H), 7.65-7.68 (m, 1H), 7.55 (s, 1H), 7.38-7.48 (m, 5H), 6.45 (d, J=5.6 Hz, 1H), 4.19 (t, J=6.9 Hz, 2H), 3.96 (s, 3H), 2.43 (t, J=6.9 Hz, 2H), 2.29-2.39 (m, 4H), 1.92-2.01 (m, 2H), 1.45-1.55 (m, 4H), 1.34-1.44 (m, 2H).

Example 6

(E)-$N^1$-(3-fluoro-4-(6-methoxy-7-(3-(pyrrolidin-1-yl)propoxy)quinoline-4-yloxy)phenyl)-$N^4$-(3-methoxybenzaldehyde)semicarbazone ESI-MS [M+H] (m/z): 587.7; $^1$H-NMR (300 MHz, DMSO) δ10.94 (s, 1H), 9.27 (s, 1H), 8.48 (d, J=5.4 Hz, 1H), 7.96 (s, 1H), 7.90-7.94 (dd, $J_1$=13.5 Hz, $J_2$=2.4 Hz, 1H), 7.62-7.67 (m, 1H), 7.59 (s, 1H), 7.46-7.50 (m, 1H), 7.32-7.44 (m, 4H), 6.96-7.00 (m, 1H), 6.45 (d, J=5.4 Hz, 1H), 4.21 (t, J=6.3 Hz, 2H), 3.96 (s, 3H), 3.83 (s, 3H), 2.67 (t, J=7.2 Hz, 2H), 2.53-2.62 (m, 4H), 1.97-2.06 (m, 2H), 1.69-1.76 (m, 4H).

Example 7

(E)-$N^1$-(3-fluoro-4-(6-methoxy-7-(3-(4-methylpiperidin-1-yl)propoxy quinoline-4-yloxy)phenyl)-$N^4$-(3-methoxybenzaldehyde)semicarbazone ESI-MS [M+H] (m/z): 616.6; $^1$H-NMR (300 MHz, DMSO) δ11.03 (s, 1H), 9.31 (s, 1H), 8.48 (d, J=5.1 Hz, 1H), 7.99 (s, 1H), 7.89-7.94 (dd, $J_1$=13.5 Hz, $J_2$=2.1 Hz, 1H), 7.63-7.71 (m, 1H), 7.59 (s, 1H), 7.47-7.54 (m, 1H), 7.34-7.44 (m, 4H), 6.97-7.04 (m, 1H), 6.45 (d, J=5.1 Hz, 1H), 4.22 (t, J=6.3 Hz, 2H), 3.95 (s, 3H), 3.85 (s, 3H), 2.95-2.99 (br s, 2H), 2.53-2.69 (m, 2H), 1.93-2.12 (m, 4H), 1.61-1.69 (m, 2H), 1.36-1.41 (br s, 1H), 1.14-1.25 (m, 2H), 0.94 (d, J=6.6 Hz, 3H).

Example 8

(E)-$N^1$-(3-fluoro-4-(6-methoxy-7-(3-(morpholin-4-yl)propoxy)quinoline-4-yloxy)phenyl)-$N^4$-(3-methoxybenzaldehyde)semicarbazone ESI-MS [M+H] (m/z): 604.7; $^1$H-NMR (300 MHz, DMSO) δ10.94 (s, 1H), 9.28 (s, 1H), 8.48 (d, J=5.1 Hz, 1H), 7.96 (s, 1H), 7.91-7.95 (dd, $J_1$=13.5 Hz, $J_2$=2.1 Hz, 1H), 7.62-7.69 (m, 1H), 7.58 (s, 1H), 7.46-7.51 (m, 1H), 7.33-7.45 (m, 4H), 6.96-7.01 (m, 1H), 6.44 (d, J=5.1 Hz, 1H), 4.21 (t, J=6.3 Hz, 2H), 3.96 (s, 3H), 3.83 (s, 3H), 3.55-3.63 (m, 4H), 2.43-2.49 (m, 2H), 2.33-2.43 (m, 4H), 1.93-2.04 (m, 2H).

Example 9

(E)-N$^1$-(3-fluoro-4-(6-methoxy-7-(3-(piperidin-1-yl)propoxy)quinoline-4-yloxy)phenyl)-N$^4$-(3-methoxybenzaldehyde)semicarbazone ESI-MS [M+H] (m/z): 602.6; $^1$H-NMR (300 MHz, DMSO) δ10.93 (s, 1H), 9.26 (s, 1H), 8.48 (d, J=5.1 Hz, 1H), 7.96 (s, 1H), 7.91-7.95 (dd, J$_1$=13.5 Hz, J$_2$=2.4 Hz, 1H), 7.62-7.68 (m, 1H), 7.54 (s, 1H), 7.46-7.50 (m, 1H), 7.32-7.44 (m, 4H), 6.96-7.00 (m, 1H), 6.44 (d, J=5.1 Hz, 1H), 4.19 (t, J=6.6 Hz, 2H), 3.96 (s, 3H), 3.83 (s, 3H), 2.41-2.47 (m, 2H), 2.30-2.39 (m, 4H), 1.90-2.01 (m, 2H), 1.45-1.55 (m, 4H), 1.34-1.44 (m, 2H).

Example 10

(E)-N$^1$-(3-fluoro-4-(6-methoxy-7-(3-(4-methylpiperidin-1-yl)propoxy)quinoline-4-lyoxy)phenyl)-N$^4$-(4-fluorobenzaldehyde)semicarbazone ESI-MS [M+H] (m/z): 604.8; $^1$H-NMR (300 MHz, DMSO) δ11.11 (s, 1H), 9.34 (s, 1H), 8.48 (d, J=5.1 Hz, 1H), 7.97 (s, 1H), 7.87-7.95 (m, 3H), 7.61-7.68 (m, 1H), 7.56 (s, 1H), 7.36-7.45 (m, 2H), 7.28 (m, 2H), 6.46 (d, J=5.1 Hz, 1H), 4.22 (t, J=6.3 Hz, 2H), 3.96 (s, 3H), 2.95-2.99 (br s, 2H), 2.52-2.64 (m, 2H), 1.95-2.13 (m, 4H), 1.61-1.67 (m, 2H), 1.36-1.44 (br s, 1H), 1.14-1.22 (m, 2H), 0.97 (d, J=6.6 Hz, 3H).

Example 11

(E)-N$^1$-(3-fluoro-4-(6-methoxy-7-(3-(piperidin-1-yl)propoxy)quinoline-4-yloxy)phenyl)-N$^4$-(4-fluorobenzaldehyde)semicarbazone ESI-MS [M+H] (m/z): 590.7; $^1$H-NMR (300 MHz, DMSO) δ10.74-11.11 (br s, 1H), 9.14-9.45 (br s, 1H), 8.48 (d, J=5.4 Hz, 1H), 7.99 (s, 1H), 7.86-7.97 (m, 3H), 7.61-7.68 (m, 1H), 7.54 (s, 1H), 7.36-7.45 (m, 2H), 7.28 (m, 2H), 6.46 (d, J=5.4 Hz, 1H), 4.19 (t, J=6.6 Hz, 2H), 3.96 (s, 3H), 2.43 (t, J=7.2 Hz, 2H), 2.27-2.39 (br s, 4H), 1.89-2.02 (m, 2H), 1.44-1.56 (m, 4H), 1.32-1.44 (m, 2H).

Example 12

(E)-N$^1$-(3-fluoro-4-(6-methoxy-7-(3-(pyrrolidin-1-yl)propoxy)quinoline-4-yloxy)phenyl)-N$^4$-(2-chloro-4-fluorobenzaldehyde)semicarbazone ESI-MS [M+H] (m/z): 611.0.

Example 13

(E)-N$^1$-(3-fluoro-4-(6-methoxy-7-(3-(4-methylpiperidin-1-yl)propoxy)quinoline-4-yloxy)phenyl)-N$^4$-(2-chloro-4-fluorobenzaldehyde)semicarbazone ESI-MS [M+H] (m/z): 639.3; $^1$H-NMR (300 MHz, DMSO) δ11.08 (s, 1H), 9.28 (s, 1H), 8.47 (d, J=5.1 Hz, 1H), 8.40-8.44 (m, 1H), 8.35 (s, 1H), 7.88-7.93 (dd, J$_1$=13.5 Hz, J$_2$=2.4 Hz, 1H), 7.59-7.65 (m, 1H), 7.48-7.56 (m, 2H), 7.32-7.43 (m, 4H), 6.44 (d, J=5.1 Hz, 1H), 4.20 (t, J=6.3 Hz, 2H), 3.96 (s, 3H), 2.93-2.98 (br s, 2H), 2.52-2.61 (m, 2H), 1.94-2.15 (m, 4H), 1.63-1.68 (m, 2H), 1.36-1.43 (br s, 1H), 1.17-1.24 (m, 2H), 0.95 (d, J=6.3 Hz, 3H).

Example 14

(E)-N$^1$-(3-fluoro-4-(6-methoxy-7-(3-(morpholin-4-yl)propoxy)quinoline-4-yloxy)phenyl)-N$^4$-(2-chloro-4-fluorobenzaldehyde)semicarbazone ESI-MS [M+H] (m/z): 627.1; $^1$H-NMR (300 MHz, DMSO) δ11.14 (s, 1H), 9.31 (s, 1H), 8.48 (d, J=5.4 Hz, 1H), 8.43-8.47 (m, 1H), 8.34 (s, 1H), 7.88-7.93 (dd, J$_1$=13.5 Hz, J$_2$=2.7 Hz, 1H), 7.59-7.67 (m, 1H), 7.50-7.56 (m, 2H), 7.32-7.45 (m, 3H), 6.46 (d, J=5.4 Hz, 1H), 4.21 (t, J=6.3 Hz, 2H), 3.98 (s, 3H), 3.58-3.63 (m, 4H), 2.43-2.49 (m, 2H), 2.35-2.43 (br s, 4H), 1.94-2.03 (m, 2H).

Example 15

(E)-N$^1$-(3-fluoro-4-(6-methoxy-7-(3-(pyrrolidin-1-yl)propoxy)quinoline-4-yloxy)phenyl)-N$^4$-(2-nitrobenzaldehyde)semicarbazone ESI-MS [M+H] (m/z): 603.8.

Example 16

(E)-N$^1$-(3-fluoro-4-(6-methoxy-7-(3-(4-methylpiperidin-1-yl)propoxy)quinoline-4-yloxy)phenyl)-N$^4$-(2-nitrobenzaldehyde)semicarbazone ESI-MS [M+H] (m/z): 631.8.

Example 17

(E)-N$^1$-(3-fluoro-4-(6-methoxy-7-(3-(piperidin-1-yl)propoxy)quinoline-4-yloxy)phenyl)-N$^4$-(acetophenone)semicarbazone ESI-MS [M+H] (m/z): 586.3.

Example 18

(E)-N$^1$-(3-fluoro-4-(6-methoxy-7-(3-(pyrrolidin-1-yl)propoxy)quinoline-4-yloxy)phenyl)-N$^4$-(2-hydroxyl-1-naphthaldehyde)semicarbazone ESI-MS [M+H] (m/z): 623.8; $^1$H-NMR (300 MHz, DMSO) δ9.84 (br s, 1H), 9.05 (s, 1H), 8.48 (d, J=5.1 Hz, 1H), 8.40 (d, J=8.4 Hz, 1H), 7.81-7.92 (m, 3H), 7.52-7.63 (m, 2H), 7.34-7.50 (m, 4H), 7.24 (d, J=8.4 Hz, 1H), 6.47 (d, J=5.1 Hz, 1H), 4.22 (t, J=5.7 Hz, 2H), 3.97 (s, 3H), 2.56-2.75 (m, 6H), 2.03-2.12 (m, 2H), 1.54-1.66 (m, 4H), 1.38-1.50 (m, 2H).

Example 19

(E)-N$^1$-(3-fluoro-4-(6-methoxy-7-(3-(pyrrolidin-1-yl)propox)quinoline-4-yloxy)phenyl)-N$^4$-(2,4-dichlorobenzaldehyde)semicarbozone ESI-MS [M+H] (m/z): 627.4; $^1$H-NMR (300 MHz, DMSO) δ11.22 (s, 1H), 9.37 (s, 1H), 8.49 (d, J=5.1 Hz, 1H), 8.42 (d, J=8.4 Hz, 1H), 8.34 (s, 1H), 7.87-7.92 (dd, J$_1$=13.2 Hz, J$_2$=2.1 Hz, 1H), 7.70 (d, J=2.1 Hz, 1H), 7.61-7.65 (m, 1H), 7.59 (s, 1H), 7.52 (d, J=8.4 Hz, 1H), 7.39-7.45 (m, 2H), 6.46 (d, J=5.1 Hz, 1H), 4.24 (t, J=4.0 Hz, 2H), 3.96 (s, 3H), 2.76-2.98 (m, 6H), 2.08-2.13 (m, 2H), 1.78-1.84 (m, 4H).

Example 20

(E)-N$^1$-(3-fluoro-4-(6-methoxy-7-(3-(morpholin-4-yl)propoxy)quinoline-4-yloxy)phenyl)-N$^4$-(2,4-dichlorobenzaldehyde)semicarbazone ESI-MS [M+H] (m/z): 643.7; $^1$H-NMR (300 MHz, DMSO) δ11.20 (s, 1H), 9.34 (s, 1H), 8.49 (d, J=5.1 Hz, 1H), 8.43 (d, J=8.7 Hz, 1H), 8.34 (s, 1H), 7.86-7.93 (dd, J$_1$=13.5 Hz, J$_2$=2.4 Hz, 1H), 7.70 (d, J=2.4 Hz, 1H), 761-7.67 (m, 1H), 7.56 (s, 1H), 7.50-7.54 (dd, J$_1$=8.7 Hz, J$_2$=2.4 Hz, 1H), 7.40-7.46 (m, 2H), 6.47 (d, J=5.1 Hz, 1H), 4.24 (t, J=6.0 Hz, 2H), 3.97 (s, 3H), 3.64-3.74 (m, 4H), 2.63-2.93 (br s, 6H), 2.05-2.18 (m, 2H).

Example 21

(E)-N$^1$-(3-fluoro-4-(6-methoxy-7-(3-(4-methylpiperidin-1-yl)propoxy)quinoline-4-yloxy)phenyl)-N$^4$-(2-hydroxy-1-naphthaldehyde)semicarbazone ESI-MS [M+H] (m/z): 652.8; $^1$H-NMR (300 MHz, DMSO) δ11.01 (s, 1H), 9.84 (s, 1H), 9.05 (s, 1H), 8.48 (d, J=5.1 Hz, 1H), 8.40 (d, J=8.7 Hz, 1H), 7.81-7.92 (m, 3H), 7.52-7.63 (m, 2H), 7.34-7.50 (m, 4H), 7.24 (d, J=8.7 Hz, 1H), 6.47 (d, J=5.1 Hz, 1H), 4.22 (t, J=5.7 Hz, 2H), 3.97 (s, 3H), 2.93-2.99 (br s, 2H), 2.52-2.59 (m, 2H), 1.92-2.10 (m, 4H), 1.65-1.69 (m, 2H), 1.36-1.44 (br s, 1H), 1.17-1.23 (m, 2H), 0.97 (d, J=6.3 Hz, 3H).

Example 22

(E)-N$^1$-(3-fluoro-4-(6-methoxy-7-(3-(pyrrolidin-1-yl)propoxy)quinoline-4-lyoxy)phenyl)-N$^4$-(3,4-difluorobenzaldehyde)semicarbazone ESI-MS [M+H] (m/z): 594.8; $^1$H-NMR (300 MHz, DMSO) δ11.18 (s, 1H), 9.41 (s, 1H), 8.48 (d, J=5.1 Hz, 1H), 8.11-8.18 (m, 1H), 7.97 (s, 1H), 7.89-7.94 (dd, J$_1$=13.5 Hz, J$_2$=2.4 Hz, 1H), 7.73-7.85 (m, 1H), 7.61-7.67 (m, 2H), 7.55 (s, 1H), 7.38-7.52 (m, 2H), 6.46 (d, J=5.1 Hz, 1H), 4.24 (t, J=6.3 Hz, 2H), 3.95 (s, 3H), 2.73-2.91 (m, 6H), 2.06-2.15 (m, 2H), 1.70-1.86 (m, 4H).

Example 23

(E)-N$^1$-(3-fluoro-4-(6-methoxy-7-(3-(morpholin-4-yl)propoxy)quinoline-4-oxy)phenyl)-N$^4$-(3,4-difluorobenzaldehyde)semicarbazone ESI-MS [M+H] (m/z): 619.6; $^1$H-NMR (300 MHz, DMSO) δ11.05 (s, 1H), 9.27 (s, 1H), 8.49 (d, J=5.1 Hz, 1H), 8.14-8.22 (m, 1H), 7.96 (s, 1H), 7.89-7.94 (dd, J$_1$=13.5 Hz, J$_2$=2.4 Hz, 1H), 7.60-7.68 (m, 2H), 7.55 (s, 1H), 7.40-7.52 (m, 3H), 6.46 (d, J=5.4 Hz, 1H), 4.21 (t, J=6.3 Hz, 2H), 3.96 (s, 3H), 3.58-3.62 (m, 4H), 2.45-2.48 (m, 2H), 2.35-2.43 (br s, 4H), 1.95-2.04 (m, 2H).

Example 24

(E)-N$^1$-(3-fluoro-4-(6-methoxy-7-(3-(pyrrolidin-1-yl)propoxy)quinoline-4-yloxy)phenyl)-N$^4$-(3-trifluoromethylbenzaldehyde)semicarbazone ESI-MS [M+H] (m/z): 626.8.

Example 25

(E)-N$^1$-(3-fluoro-4-(6-methoxy-7-(3-(4-methylpiperidin-1-yl)propoxy)quinoline-4-yloxy)phenyl)-N$^4$-(2,4-difluorobenzaldehyde) semicarbazone ESI-MS [M+H] (m/z): 622.7.

Example 26

(E)-N$^1$-(3-fluoro-4-(6-methoxy-7-(3-(morpholin-4-yl)propoxy)quinoline-4-yloxy)phenyl)-N$^4$-(3-trifluoromethylbenzaldehyde)semicarbazone ESI-MS [M+H] (m/z): 642.8; $^1$H-NMR (300 MHz, DMSO) δ11.10 (s, 1H), 9.38 (s, 1H), 8.49 (d, J=5.4 Hz, 1H), 8.26 (s, 1H), 8.18 (d, J=8.1 Hz, 1H), 8.08 (s, 1H), 7.90-7.95 (dd, J$_1$=13.5 Hz, J$_2$=2.1 Hz, 1H), 7.63-7.78 (m, 3H), 7.55 (s, 1H), 7.40-7.46 (m, 2H), 6.46 (d, J=5.1 Hz, 1H), 4.21 (t, J=6.3 Hz, 2H), 3.97 (s, 3H), 3.58-3.62 (m, 4H), 2.44-2.48 (m, 2H), 2.33-2.42 (br s, 4H), 1.96-2.05 (m, 2H).

Example 27

(E)-N$^1$-(3-fluoro-4-(6-methoxy-7-(3-(morpholin-4-yl)propoxy)quinoline-4-yloxy)phenyl)-N$^4$-(3,5-dimethyl-4-hydroxybenzaldehyde)semicarbazone ESI-MS [M+H] (m/z): 617.9; $^1$H-NMR (300 MHz, DMSO) δ10.66 (s, 1H), 9.11 (s, 1H), 8.64 (s, 1H), 8.48 (d, J=5.1 Hz, 1H), 7.91-7.97 (dd, J$_1$=13.5 Hz, J$_2$=2.4 Hz, 1H), 7.83 (s, 1H), 7.64-7.68 (m, 1H), 7.55 (s, 1H), 7.37-7.42 (m, 4H), 6.45 (d, J=5.1 Hz, 1H), 4.21 (t, J=6.3 Hz, 2H), 3.96 (s, 3H), 3.58-3.61 (m, 4H), 2.40-2.47 (m, 2H), 2.34-2.44 (br s, 4H), 2.21 (s, 6H), 1.94-2.04 (m, 2H).

Example 28

(E)-N$^1$-(3-fluoro-4-(6-methoxy-7-(3-(morpholin-4-yl)propoxy)quinoline-4-yloxy)phenyl)-N$^4$-(2-hydroxyl-1-naphthaldehyde)semicarbazone ESI-MS [M+H] (m/z): 640.7.

Example 29

(E)-N$^1$-(3-fluoro-4-(6-methoxy-7-(3-(pyrrolidin-1-yl)propoxy)quinoline-4-yloxy)phenyl)-N$^4$-(3-allyl-2-hydroxybenzaldehyde)semicarbazone ESI-MS [M+H] (m/z): 614.9; $^1$H-NMR (300 MHz, DMSO) δ11.09 (s, 1H), 9.84 (s, 1H), 8.51 (d, J=5.4 Hz, 1H), 8.28 (s, 1H), 7.89 (d, J=12.3 Hz, 1H), 7.58 (s, 1H), 7.45-7.39 (m, 4H), 7.14 (d, J=7.2 Hz, 1H), 6.88 (t, J=7.2 Hz, 1H), 6.51 (d, J=4.8 Hz, 1H), 5.93-6.07 (m, 1H), 5.02-5.10 (m, 2H), 4.28 (t, J=5.7 Hz, 2H), 3.98 (s, 3H), 3.25 (m, 2H), 2.63 (t, J=6.9 Hz, 2H), 2.45-2.54 (m, 4H), 1.99-2.07 (m, 2H), 1.65-1.77 (m, 4H).

Example 30

(E)-N$^1$-(3-fluoro-4-(6-methoxy-7-(3-(piperidin-1-yl)propoxy)quinoline-4-yloxy)phenyl)-N$^4$-(propiophenone)thiosemicarbazone ESI-MS [M+H] (m/z): 600.3.

Step L: 4-(2-fluoro-4-isothiocyanatophenoxy)-6-methoxy-7-(3-(piperidin-1-yl)propoxy)quinolone (XII)

Intermediate X 10 g (23.5 mmol) was dissolved in $CH_2Cl_2$ (100 mL) and sat. aq. $NaHCO_3$ (20 mL) was added. The resulting biphasic solution was cooled to 0° C. and thiophosgene 2.2 mL (28.2 mmol) was then carefully added via syringe. After the addition was completed, the reaction was allowed to warm to room temperature and stirred for 6 h. The organic layer was separated and the aqueous layer was extracted with $CH_2Cl_2$. The combined organic layers were dried over Na2SO4, filtered, and concentrated under reduced pressure to afford intermediate XII (8.14 g) as a yellow oil, yield: 74.1%.

Step L: 4-(4-(7-(3-(piperidin-1-yl)propoxy)-6-methoxyquinolin-4-yloxy)-3-fluorophenyl)thiosemicarbazide (A-2)

To a solution of intermediate XII 6 g (12.8 mmol) in $CH_2Cl_2$ (40 mL) was added 80% hydrazine monohydrate 30 mL), and the biphasic solution was vigorously stirred for 12 h at room temperature. The organic layer was separated and washed with water (3×20 mL). The combined organic layers were dried over $Na_2SO_4$, filtered, and concentrated under reduced pressure to afford A-2 (4.5 g) as a yellow solid, yield: 69.5%.

Step N: (E)-$N^1$-(3-fluoro-4-(6-methoxy-7-(3-(piperidin-1-yl)propoxy)quinolin-4-yloxy)phenyl)-$N^4$-(3,4-difluorobenzylidene)thiosemicarbazide Example 31

To a solution of A-7 0.2 g (0.40 mmol) in isopropanol (2 mL), 2,4-difluorobenzylidene 0.07 g (0.50 mmol) and acetic acid (1 drop) were added, and the mixture was refluxed for 6 h. The resultant precipitate was filtered and washed with a little amount of isopropanol to afford the target compound 0.13 g as a yellow solid, yield: 52.2%.

ESI-MS [M+H] (m/z): 607.7; $^1$H-NMR (300 MHz, DMSO) δ11.08 (s, 1H), 9.34 (s, 1H), 8.47 (d, J=5.1 Hz, 1H), 8.09-8.17 (m, 1H), 7.96 (s, 1H), 7.86-7.92 (dd, $J_1$=13.5 Hz, $J_2$=2.4 Hz, 1H), 7.73-7.84 (m, 1H), 7.60-7.66 (m, 2H), 7.52 (s, 1H), 7.38-7.50 (m, 2H), 6.46 (d, J=5.1 Hz, 1H), 4.22 (t, J=6.3 Hz, 2H), 3.94 (s, 3H), 2.41-2.45 (m, 2H), 2.33-2.39 (m, 4H), 1.90-1.98 (m, 2H), 1.45-1.54 (m, 4H), 1.34-1.42 (m, 2H).

According to the methods in example 31, examples 32-45 can be obtained by condensation reaction between varies substituted intermediates A-1 and corresponding aldehydes.

Example 32

(E)-$N^1$-(3-fluoro-4-(6-methoxy-7-(3-(pyrrolidin-1-yl)propoxy)quinoline-4-yloxy)phenyl))-$N^4$-(2-nitrobenzaldehyde)thiosemicarbazone ESI-MS [M+H] (m/z): 620.0.

Example 33

(E)-$N^1$-(3-fluoro-4-(6-methoxy-7-(3-(morpholin-4-yl)propoxy)quinoline-4-yloxy)phenyl)-$N^4$-(2-nitrobenzaldehyde)thiosemicarbazone ESI-MS [M+H] (m/z): 635.8; $^1$H-NMR (300 MHz, DMSO) δ11.25 (s, 1H), 9.28 (s, 1H), 8.47-8.51 (m, 2H), 8.40 (m, 1H), 8.06 (d, J=8.1 Hz, 1H), 7.87-7.93 (dd, $J_1$=13.5 Hz, $J_2$=2.1 Hz, 1H), 7.78-7.84 (m, 1H), 7.65 (d, J=8.1 Hz, 1H), 7.61-7.63 (m, 1H), 7.54 (s, 1H), 7.42-7.46 (m, 1H), 7.40 (s, 1H), 6.47 (d, J=5.1 Hz, 1H), 4.22 (t, J=6.0 Hz, 2H), 3.96 (s, 3H), 3.55-3.61 (m, 4H), 2.42-2.47 (m, 2H), 2.32-2.41 (br s, 4H), 1.95-2.05 (m, 2H).

Example 34

(E)-$N^1$-(3-fluoro-4-(6-methoxy-7-(3-(piperidin-1-yl)propoxy)quinoline-4-yloxy)phenyl)-$N^4$-(2-nitrobenzaldehyde)thiosemicarbazone ESI-MS [M+H] (m/z): 635.6.

Example 35

(E)-$N^1$-(3-fluoro-4-(6-methoxy-7-(3-(morpholin-4-yl)propoxy)quinoline-4-yloxy)phenyl)-$N^4$-(3-allyl-2-hydroxybenzaldehyde)thiosemicarbazone ESI-MS [M+H] (m/z): 630.6.

Example 36

(E)-$N^1$-(3-fluoro-4-(6-methoxy-7-(3-(pyrrolidin-1-yl)propoxy)quinoline-4-yloxy)phenyl)-$N^4$-(benzaldehyde)thiosemicarbazone ESI-MS [M+H] (m/z): 574.5; $^1$H-NMR (300 MHz, DMSO) δ10.89 (s, 1H), 9.21 (s, 1H), 8.47 (d, J=5.1 Hz, 1H), 7.97 (s, 1H), 7.88-7.95 (dd, $J_1$=13.5 Hz, $J_2$=2.4 Hz, 1H), 7.81-7.85 (m, 2H), 7.64-7.68 (m, 1H), 7.57 (s, 1H), 7.39-7.48 (m, 5H), 6.46 (d, J=5.1 Hz, 1H), 4.20 (t, J=6.3 Hz, 2H), 3.95 (s, 3H), 2.55 (t, J=6.9 Hz, 2H), 2.41-2.52 (m, 4H), 1.93-2.04 (m, 2H), 1.61-1.70 (m, 4H).

Example 37

(E)-$N^1$-(3-fluoro-4-(6-methoxy-7-(3-(4-methylpiperidin-1-yl)propoxy)quinoline-4-yloxy)phenyl)-$N^4$-(benzaldehyde)thiosemicarbazone ESI-MS [M+H] (m/z): 602.8.

Example 38

(E)-$N^1$-(3-fluoro-4-(6-methoxy-7-(3-(morpholin-4-yl)propoxy)quinoline-4-yloxy)phenyl)-$N^4$-(benzaldehyde)thiosemicarbazone ESI-MS [M+H] (m/z): 590.8; $^1$H-NMR (300 MHz, DMSO) δ10.88 (s, 1H), 9.26 (s, 1H), 8.45 (d, J=5.1 Hz, 1H), 8.05 (s, 1H), 7.92-7.98 (dd, $J_1$=13.5 Hz, $J_2$=2.1 Hz, 1H), 7.84-7.88 (m, 2H), 7.65-7.68 (m, 1H), 7.57 (s, 1H), 7.36-7.49 (m, 5H), 6.46 (d, J=5.4 Hz, 1H), 4.20 (t, J=6.3 Hz, 2H), 3.95 (s, 3H), 3.59-3.62 (m, 4H), 2.44-2.49 (m, 2H), 2.33-2.42 (br s, 4H), 1.94-2.02 (m, 2H).

Example 39

(E)-$N^1$-(3-fluoro-4-(6-methoxy-7-(3-(4-methyl-1-piperazinyl)propoxy)quinoline-4-yloxy)phenyl)-$N^4$-(benzaldehyde)thiosemicarbazone ESI-MS [M+H] (m/z): 603.6; $^1$H-NMR (300 MHz, DMSO) δ10.93 (s, 1H), 9.26 (s, 1H), 8.46 (d, J=5.1 Hz, 1H), 8.02 (s, 1H), 7.88-7.95 (dd, $J_1$=13.5 Hz, $J_2$=2.1 Hz, 1H), 7.79-7.84 (m, 2H), 7.63-7.71 (m, 1H), 7.60 (s, 1H), 7.41-7.47 (m, 5H), 6.45 (d, J=5.1 Hz, 1H), 4.23 (d, J=6.3 Hz, 2H), 3.96 (s, 3H), 3.37-3.49 (m, 10H), 2.88 (s, 3H), 2.35 (s, 2H).

Example 40

(E)-$N^1$-(3-fluoro-4-(6-methoxy-7-(3-(4-methyl-1-piperazinyl)propoxy)quinoline-4-yloxy)phenyl)-$N^4$-(2,4-dichlorobenzaldehyde)thiosemicarbazone ESI-MS [M+H] (m/z): 672.6; $^1$H-NMR (300 MHz, DMSO) δ10.96 (s, 1H), 9.40 (s, 1H), 8.48 (d, J=5.1 Hz, 1H), 8.35-8.42 (d, J=8.7 Hz, 1H), 8.26 (s, 1H), 7.83-7.91 (dd, $J_1$=13.5 Hz, $J_2$=2.1 Hz, 1H), 7.66 (d, J=2.1 Hz, 1H), 7.58-7.63 (m, 1H), 7.52 (s, 1H), 7.45-7.51 (dd, $J_1$=8.7 Hz, $J_2$=2.1 Hz, 1H), 7.36-7.42 (m, 2H), 6.46 (d, J=5.1 Hz, 1H), 4.22 (t, J=6.0 Hz, 2H), 3.94 (s, 3H), 3.35-3.44 (m, 10H), 2.87 (s, 3H), 2.33 (s, 2H).

Example 41

(E)-$N^1$-(3-fluoro-4-(6-methoxy-7-(3-(piperidin-1-yl)propoxy)quinoline-4-yloxy)phenyl)-$N^4$-(2,4-dichlorobenzaldehyde)thiosemicarbazone ESI-MS [M+H] (m/z): 641.6; $^1$H-NMR (300 MHz, DMSO) δ11.05 (s, 1H), 9.45 (s, 1H), 8.47 (d, J=5.1 Hz, 1H), 8.39-8.43 (d, J=8.7 Hz, 1H), 8.32 (s, 1H), 7.86-7.93 (dd, $J_1$=13.5 Hz, $J_2$=2.4 Hz, 1H), 7.68 (d, J=2.4 Hz, 1H), 7.61-7.65 (m, 1H), 7.54 (s, 1H), 7.47-7.52 (dd, $J_1$=8.7 Hz, $J_2$=2.4 Hz, 1H), 7.38-7.44 (m, 2H), 6.45 (d, J=5.1 Hz, 1H), 4.19 (t, J=6.0 Hz, 2H), 3.95 (s, 3H), 2.38-2.45 (m, 2H), 2.29-2.35 (m, 4H), 1.90-1.99 (m, 2H), 1.43-1.52 (m, 4H), 1.32-1.41 (m, 2H).

Example 42

(E)-$N^1$-(3-fluoro-4-(6-methoxy-7-(3-(4-methyl-1-piperazinyl)propoxy)quinoline-4-yloxy)phenyl)-$N^4$-(2-chloro-4-fluorobenzaldehyde)thiosemicarbazone ESI-MS [M+H] (m/z): 655.9; $^1$H-NMR (300 MHz, DMSO) δ11.01 (s, 1H), 9.29 (s, 1H), 8.49 (d, J=5.1 Hz, 1H), 8.39-8.44 (m, 1H), 8.36 (s, 1H), 7.89-7.95 (dd, $J_1$=13.5 Hz, $J_2$=2.7 Hz, 1H), 7.58-7.70 (m, 1H), 7.47-7.54 (m, 2H), 7.35-7.43 (m, 3H), 6.46 (d, J=5.1 Hz, 1H), 4.20 (t, J=6.3 Hz, 2H), 3.97 (s, 3H), 3.37-3.47 (m, 10H), 2.89 (s, 3H), 2.36 (s, 2H).

Example 43

(E)-$N^1$-(3-fluoro-4-(6-methoxy-7-(3-(piperidin-1-yl)propoxy)quinoline-4-yloxy)phenyl)-$N^4$-(2-chloro-4-fluorobenzaldehyde)thiosemicarbazone ESI-MS [M+H] (m/z): 625.1; $^1$H-NMR (300 MHz, DMSO) δ10.97 (s, 1H), 9.26 (s, 1H), 8.46 (d, J=5.4 Hz, 1H), 8.39-8.44 (m, 1H), 8.32 (s, 1H), 7.88-7.93 (dd, $J_1$=13.5 Hz, $J_2$=2.7 Hz, 1H), 7.57-7.68 (m, 1H), 7.47-7.54 (m, 2H), 7.32-7.41 (m, 3H), 6.46 (d, J=5.4 Hz, 1H), 4.18 (t, J=6.3 Hz, 2H), 3.94 (s, 3H), 2.38-2.46 (m, 2H), 2.30-2.37 (m, 4H), 1.92-1.99 (m, 2H), 1.43-1.55 (m, 4H), 1.31-1.39 (m, 2H).

Example 44

(E)-$N^1$-(3-fluoro-4-(6-methoxy-7-(3-(pyrrolidin-1-yl)propoxy)quinoline-4-yloxy)phenyl)-$N^4$-(4-fluorobenzaldehyde)thiosemicarbazone ESI-MS [M+H] (m/z): 592.7; $^1$H-NMR (300 MHz, DMSO) δ10.91 (s, 1H), 9.20 (s, 1H), 8.48 (d, J=5.1 Hz, 1H), 7.99 (s, 1H), 7.89-7.98 (m, 3H), 7.63-7.66 (m, 1H), 7.55 (s, 1H), 7.41 (d, J=9.0 Hz, 2H), 7.28 (d, J=9.0 Hz, 2H), 6.46 (d, J=5.1 Hz, 1H), 4.23 (t, J=6.0 Hz, 2H), 3.97 (s, 3H), 2.60-2.85 (m, 6H), 2.01-2.10 (m, 2H), 1.70-1.85 (m, 4H).

Example 45

(E)-$N^1$-(3-fluoro-4-(6-methoxy-7-(3-(morpholin-4-yl)propoxy)quinoline-4-yloxy)phenyl)-$N^4$-(4-fluorobenzaldehyde)thiosemicarbazone ESI-MS [M+H] (m/z): 608.8.

Step O: 3-Fluoro-4-(6-methoxy-7-(3-(piperidin-1-yl)propoxy)-quinolin-4-yloxy)benzaldehyde (B)

To dry chlorobenzene (240 mL) was added 3-fluoro-4-hydroxybenzaldehyde 37.6 g (0.27 mol), then intermediate VII was added at 140° C. and reacted for 23 h. After cooling to room temperature, the reaction mixture was concentrated under reduced pressure to yield a pale brown solid. The solid was dissolved in $CH_2Cl_2$, and washed with saturated $K_2CO_3$ aqueous solution, and dried over anhydrous $Na_2SO_4$, concentrated under reduced pressure and recrystallization from ethanol to afford corresponding benzaldehyde (54.6 g), yield: 69.6%.

Step P: phenyl(4-chloro-3-(trifluoromethyl)phenyl)carbamate (W-1)

To the mixture of 4-chloro-3-(trifluoromethyl)aniline 10 g (0.05 mol) and $K_2CO_3$ 14.1 g (0.10 mol) in dry acetone (100 mL), phenyl chloroformate 7.5 mL (0.06 mol) was added dropwise while maintaining the temperature between 0 and 5° C. After the addition was completed, the mixture was warmed to room temperature for another 1.5 h, and the solvent was evaporated under reduced pressure. The residue was washed with water, filtered, and dried under vacuum to afford corresponding compound 14.8 g as a white solid, yield: 93.7%.

Step Q: N-(4-chloro-3-(trifluoromethyl)phenyl)hydrazinecarboxamide (W-2)

A mixture of an intermediate W-1 4 g (13.6 mmol) and 80% hydrazine hydrate (20 mL) in 1,4-dioxane (30 mL) was refluxed for 4 h with vigorous agitation. After cooling to room temperature, the solvent was evaporated under reduced pressure. And the resulting precipitate was filtered-off to afford corresponding semicarbazides 3.0 g, 86.4%.

Step R: (E)-$N^1$-(4-chloro-3-(trifluoromethyl)phenyl)-$N^4$-(3-fluoro-4-(6-methoxy-7-(3-(piperidin-1-yl)propoxy)quinolin-4-yloxy)benzylidene)-semicarbazide Example 46

To a solution of W-2 0.12 g (0.48 mmol) in isopropanol (2 mL), 0.2 g (0.46 mmol) B and acetic acid (1 drop) were added, and the mixture was refluxed for 7 h. The resultant precipitate was filtered and washed with a little amount of isopropanol to afford the target compound 0.24 g as a white solid, yield: 74.8%.

ESI-MS [M+H] (m/z): 675.1; $^1$H-NMR (300 MHz, DMSO) δ11.17 (s, 1H), 9.45 (s, 1H), 8.50 (d, J=5.4 Hz, 1H), 8.27 (d, J=2.7 Hz, 1H), 8.19 (dd, $J_1$=12.0 Hz, $J_2$=1.6 Hz, 1H), 8.02-8.06 (m, 2H), 7.72-7.77 (m, 1H), 7.66 (d, J=9.0 Hz, 1H), 7.49-7.54 (m, 2H), 7.42 (s, 1H), 6.52 (d, J=5.4 Hz, 1H), 4.21 (t, J=6.3 Hz, 2H), 3.96 (s, 3H), 2.53-2.60 (m, 2H), 2.39-2.48 (br s, 4H), 1.97-2.06 (m, 2H), 1.52-1.59 (m, 4H), 1.36-1.46 (m, 2H).

According to the methods in example 46, example 47-60 can be obtained by condensation reaction between varies substituted intermediate B and corresponding semicarbazides.

Example 47

(E)-$N^1$-(2-fluorophenyl)-$N^4$-(3-fluoro-4-(6-methoxy-7-(3-(piperidin-1-yl)propoxy)quinoline-4-yloxy)benzaldehyde)semicarbazone ESI-MS [M+H] (m/z): 590.7; $^1$H-NMR (300 MHz, DMSO) δ11.08 (s, 1H), 8.87 (s, 1H), 8.50 (d, J=5.1 Hz, 1H), 8.08 (d, J=12.0 Hz, 1H), 8.02 (s, 1H), 7.72-7.76 (m, 1H), 7.68 (d, J=12.0 Hz, 1H), 7.48-7.53 (m, 2H), 7.42 (s, 1H), 7.22-7.30 (m, 1H), 7.13-7.20 (m, 2H), 6.53 (d, J=5.1 Hz, 1H), 4.21 (t, J=6.3 Hz, 2H), 3.96 (s, 3H), 2.53-2.71 (m, 6H), 2.00-2.09 (m, 2H), 1.52-1.65 (m, 4H), 1.36-1.50 (m, 2H).

Example 48

(E)-$N^1$-(3,5-dichlorophenyl)-$N^4$-(3-fluoro-4-(6-methoxy-7-(3-(piperidin-1-yl)propoxy)quinoline-4-yloxy)benzaldehyde)semicarbazone ESI-MS [M+H] (m/z): 641.7; $^1$H-NMR (300 MHz, DMSO) δ11.18 (s, 1H), 9.31 (s, 1H), 8.52 (d, J=5.1 Hz, 1H), 8.21 (dd, $J_1$=12.0 Hz, $J_2$=1.8 Hz, 1H), 8.03 (s, 1H), 7.87 (s, 1H), 7.86 (s, 1H), 7.49-7.60 (m, 3H), 7.30 (m, 1H), 7.22 (t, J=1.8 Hz, 1H), 6.54 (d, J=5.1 Hz, 1H), 4.28 (t, J=6.0 Hz, 2H), 3.97 (s, 3H), 3.42-3.56 (m, 2H), 3.16-3.25 (m, 2H), 2.77-3.00 (br s, 2H), 2.25-2.36 (m, 2H), 1.74-1.86 (m, 4H), 1.30-1.55 (br s, 2H).

Example 49

(E)-$N^1$-(3,5-dimethoxyphenyl)-$N^4$-(3-fluoro-4-(6-methoxy-7-(3-(piperidin-1-yl)propoxy)quinoline-4-yloxy)benzaldehyde)semicarbazone ESI-MS [M+H] (m/z): 632.6; $^1$H-NMR (300 MHz, DMSO) δ10.96 (s, 1H), 8.98 (s, 1H), 8.61 (d, J=5.4 Hz, 1H), 8.22 (dd, $J_1$=12.0 Hz, $J_2$=1.8 Hz, 1H), 8.03 (s, 1H), 7.52-7.57 (m, 2H), 7.45 (d, J=8.7 Hz, 1H), 7.42 (s, 1H), 6.99 (s, 1H), 6.98 (s, 1H), 6.67 (d, J=5.4 Hz, 1H), 6.19 (t, J=1.8 Hz, 1H), 4.30 (t, J=6.3 Hz, 2H), 3.99 (s, 3H), 3.73 (s, 6H), 3.47-3.51 (m, 2H), 3.18-3.22 (m, 2H), 2.85-2.93 (m, 2H), 2.29-2.39 (m, 2H), 1.68-1.91 (m, 6H).

Example 50

(E)-$N^1$-(3-fluoro-6-methylphenyl)-$N^4$-(3-fluoro-4-(6-methoxy-7-(3-(piperidin-1-yl)propoxy)quinoline-4-yloxy)benzaldehyde)semicarbazone ESI-MS [M+H] (m/z): 604.6.

Example 51

(E)-$N^1$-(4-chloro-3-(trifluoromethyl)phenyl)-$N^4$-(3-fluoro-4-(6-methoxy-7-(3-(4-methyl-1-piperazinyl)propoxy)quinoline-4-yloxy)benzaldehyde)semicarbazone ESI-MS [M+H] (m/z): 690.1; $^1$H-NMR (300 MHz, DMSO) δ11.05 (s, 1H), 9.40 (s, 1H), 8.39 (d, J=5.1 Hz, 1H), 8.24 (d, J=2.7 Hz, 1H), 8.15 (dd, $J_1$=12.0 Hz, $J_2$=1.6 Hz, 1H), 8.00-8.05 (m, 2H), 7.71-7.75 (m, 1H), 7.62 (d, J=9.0 Hz, 1H), 7.46-7.51 (m, 2H), 7.40 (s, 1H), 6.46 (d, J=5.1 Hz, 1H), 4.22 (t, J=6.0 Hz, 2H), 3.94 (s, 3H), 3.35-3.44 (m, 10H), 2.87 (s, 3H), 2.33 (s, 2H).

Example 52

(E)-$N^1$-phenyl-$N^4$-(3-fluoro-4-(6-methoxy-7-(3-(4-methyl-1-piperazin yl)propoxy)quinoline-4-yloxy)benzaldehyde)semicarbazone ESI-MS [M+H] (m/z): 587.6.

Example 53

(E)-$N^1$-(4-chlorophenyl)-$N^4$-(3-fluoro-4-(6-methoxy-7-(3-(4-methyl-1-piperazinyl)propoxy)quinoline-4-yloxy)benzaldehyde)semicarbazone ESI-MS [M+H] (m/z): 622.2.

Example 54

(E)-$N^1$-(3-bromophenyl)-$N^4$-(3-fluoro-4-(6-methoxy-7-(3-(morpholin-4-yl)propoxy)quinoline-4-yloxy)benzaldehyde)semicarbazone ESI-MS [M+H] (m/z): 653.6.

Example 55

(E)-$N^1$-phenyl-$N^4$-(3-fluoro-4-(6-methoxy-7-(3-(morpholin-4-yl)prop oxy)quinoline-4-yloxy)benzaldehyde)semicarbazone ESI-MS [M+H] (m/z): 574.7.

Example 56

(E)-$N^1$-(3,5-difluorophenyl)-$N^4$-(3-fluoro-4-(6-methoxy-7-(3-(morpholin-4-yl)propoxy)quinoline-4-yloxy)benzaldehyde)semicarbazone ESI-MS [M+H] (m/z): 610.5.

Example 57

(E)-$N^1$-(3,5-dimethoxyphenyl)-$N^4$-(3-fluoro-4-(6-methoxy-7-(3-(morpholin-4-yl)propoxy)quinoline-4-oxy)benzaldehyde)semicarbazone ESI-MS [M+H] (m/z): 634.8; $^1$H-NMR (300 MHz, DMSO) δ11.13 (s, 1H), 9.18 (s, 1H), 8.81 (d, J=5.4 Hz, 1H), 8.42 (dd, $J_1$=12.0 Hz, $J_2$=1.8 Hz, 1H), 8.18 (s, 1H), 7.65 (d, J=8.7 Hz, 1H), 7.59 (s, 1H), 7.53-7.57 (m, 2H), 7.05 (s, 1H), 7.03 (s, 1H), 6.77 (d, J=5.4 Hz, 1H), 6.39 (t, J=1.8 Hz, 1H), 4.21 (t, J=6.3 Hz, 2H), 3.93 (s, 3H), 3.76 (s, 6H), 3.68 (m, 4H), 2.41-2.47 (m, 2H), 2.35-2.46 (br s, 4H), 1.96-2.04 (m, 2H).

Example 58

(E)-N$^1$-phenyl-N$^4$-(3-fluoro-4-(6-methoxy-7-(3-(4-methylpiperidin-1-yl)propoxy)quinoline-4-yloxy)benzaldehyde)semicarbazone ESI-MS [M+H] (m/z): 586.6.

Example 59

(E)-N$^1$-(3,5-dimethoxyphenyl)-N$^4$-(3-fluoro-4-(6-methoxy-7-(3-(4-methylpiperidin-1-yl)propoxy)quinoline-4-yloxy)benzaldehyde)semicarbazone ESI-MS [M+H] (m/z): 660.9.

Example 60

(E)-N$^1$-(2-fluorophenyl)-N$^4$-(3-fluoro-4-(6-methoxy-7-(3-(4-methylpiperidin-1-yl)propoxy)quinoline-4-yloxy)benzaldehyde)semicarbazone ESI-MS [M+H] (m/z): 604.9; $^1$H-NMR (300 MHz, DMSO) δ11.09 (s, 1H), 8.87 (s, 1H), 8.51 (d, J=5.1 Hz, 1H), 8.08 (dd, J$_1$=12.3 Hz, J$_2$=1.2 Hz, 1H), 8.03 (s, 1H), 7.73-7.79 (m, 1H), 7.69 (d, J=5.1 Hz, 1H), 7.48-7.54 (m, 1H), 7.43 (s, 1H), 7.23-7.31 (m, 1H), 7.15-7.22 (m, 2H), 6.54 (d, J=5.1 Hz, 1H), 4.22 (t, J=6.3 Hz, 2H), 3.96 (s, 3H), 3.05-3.10 (m, 2H), 2.63-2.80 (br s, 2H), 2.17-2.38 (br s, 2H), 2.01-2.15 (m, 2H), 1.60-1.71 (m, 2H), 1.21-1.47 (m, 4H).

Step S: 3,5-dichloroisothiocyanatobenzene (W-3)

3,5-dichloroaniline 20 g (0.32 mol) was dissolved in CH$_2$Cl$_2$ (150 mL) and sat. aq. NaHCO$_3$ (50 mL) was added. The resulting biphasic solution was cooled to 0° C. and thiophosgene (0.38 mol) was then carefully added via syringe. After the addition was completed, the reaction was allowed to warm to room temperature and stirred for 2 h. The organic layer was separated and dried over Na$_2$SO$_4$. The filtrate was concentrated under reduced pressure to afford title compound 47.1 g as a yellow oil, yield: 72.1%.

Step T: 3,5-dichlorophenyl isothiocyanate (W-4)

To a solution of intermediate W-3 10 g (49.0 mmol) in CH$_2$Cl$_2$ (100 mL) was added 80% hydrazine monohydrate (50 mL), and the biphasic solution was vigorously stirred for 10 h at room temperature. The organic layer was separated and washed with water (3×20 mL). The combined organic layers were dried over Na$_2$SO$_4$, filtered, concentrated under reduced pressure and washed with anhydrous diethyl ether, dry to constant weight to afford a paw yellow solid 8.2 g, yield: 71.0%.

Step U: (E)-N$^1$-(3,5-dichlorophenyl)-N$^4$-(3-fluoro-4-(6-methoxy-7-(3-(piperidin-1-yl)propoxy)quinolin-4-yloxy)benzylidene)thiosemicarbazide Example 61

To a solution of W-4 0.11 g (0.48 mmol) in isopropanol (2 mL), 0.2 g (0.46 mmol) B and acetic acid (1 drop) were added, and the mixture was refluxed for 8 h. The resultant precipitate was filtered and washed with a little amount of isopropanol to afford the target compound 0.22 g as a white solid, yield: 73.1%.

ESI-MS [M+H] (m/z): 641.7; $^1$H-NMR (300 MHz, DMSO) δ11.12 (s, 1H), 9.18 (s, 1H), 8.48 (d, J=5.1 Hz, 1H), 8.18 (dd, J$_1$=12.0 Hz, J$_2$=1.5 Hz, 1H), 8.00 (s, 1H), 7.83 (s, 1H), 7.81 (s, 1H), 7.49-7.57 (m, 3H), 7.32 (m, 1H), 7.24 (t, J=1.5 Hz, 1H), 6.47 (d, J=5.1 Hz, 1H), 4.25 (t, J=6.0 Hz, 2H), 3.95 (s, 3H), 3.41-3.54 (m, 2H), 3.16-3.27 (m, 2H), 2.77-2.95 (br s, 2H), 2.25-2.37 (m, 2H), 1.74-1.84 (m, 4H), 1.33-1.51 (br s, 2H).

According to the methods in example 61, example 62-68 can be obtained by condensation reaction between varies substituted intermediate B and corresponding thiosemicarbazides.

Example 62

(E)-N$^1$-(3,5-dimethoxyphenyl)-N$^4$-(4-(6-methoxy-7-(3-(piperidin-1-yl)propoxy)quinoline-4-yloxy)-3-fluorobenzaldehyde)thiosemicarbazone ESI-MS [M+H] (m/z): 648.8.

Example 63

(E)-N$^1$-phenyl-N$^4$-(3-fluoro-4-(6-methoxy-7-(3-(4-methylpiperidin-1-yl)propoxy)quinoline-4-yloxy)benzaldehyde)thiosemicarbazone ESI-MS [M+H] (m/z): 586.8; $^1$H-NMR (300 MHz, DMSO) δ11.21 (s, 1H), 9.52 (s, 1H), 8.57 (d, J=5.4 Hz, 1H), 8.04 (s, 1H), 7.92-7.99 (dd, J$_1$=13.5 Hz, J$_2$=2.1 Hz, 1H), 7.84-7.89 (m, 2H), 7.66-7.73 (m, 1H), 7.59 (s, 1H), 7.38-7.48 (m, 5H), 6.46 (d, J=5.4 Hz, 1H), 4.21 (t, J=6.3 Hz, 2H), 3.95 (s, 3H), 2.92-2.99 (br s, 2H), 2.56-2.68 (m, 2H), 1.92-2.14 (m, 4H), 1.58-1.69 (m, 2H), 1.39 (br s, 1H), 1.11-1.27 (m, 2H), 0.95 (d, J=6.6 Hz, 3H).

Example 64

(E)-N$^1$-[4-chloro-3-(trifluoromethyl)phenyl]-N$^4$-(3-fluoro-4-(6-methoxy-7-(3-(4-methylpiperidin-1-yl)propoxy)quinoline-4-yloxy)benzaldehyde)thiosemicarbazone ESI-MS [M+H] (m/z): 705.4.

Example 65

(E)-N$^1$-(3-bromophenyl)-N$^4$-(3-fluoro-4-(6-methoxy-7-(3-(morpholin-4-yl)propoxy)quinoline-4-yloxy)benzaldehyde)thiosemicarbazone ESI-MS [M+H] (m/z): 669.7.

Example 66

(E)-N$^1$-(3,5-difluorophenyl)-N$^4$-(3-fluoro-4-(6-methoxy-7-(3-(morpholin-4-yl)propoxy)quinoline-4-yloxy)benzaldehyde)thiosemicarbazone ESI-MS [M+H] (m/z): 625.8.

Example 67

(E)-$N^1$-phenyl-$N^4$-(3-fluoro-4-(6-methoxy-7-(3-(4-methyl-1-piperazinyl)propoxy)quinoline-4-yloxy)benzaldehyde)thiosemicarbazone ESI-MS [M+H] (m/z): 602.9.

Example 68

(E)-$N^1$-(4-chlorophenyl)-$N^4$-(3-fluoro-4-(6-methoxy-7-(3-(4-methyl-1-piperazinyl)propoxy)quinoline-4-yloxy)benzaldehyde)thiosemicarbazone ESI-MS [M+H] (m/z): 637.3.

Anti-Tumor Activity of the Compounds of the Invention
In Vitro Anti-Tumor Cellular Activity The in vitro inhibitory activity of the quinoline derivatives of formula I in the invention was evaluated against the cancer cell lines H460 (human lung cancer cell), HT-29 (colon cancer cell), MKN-45 (human gastric carcinoma cell), SMMC-7721 (hepatoma cell), MDA-MB-231 (human beast cancer cell), U87MG (Human malignant glioblastoma cell).

(1) After recovery and passaged 2-3 times stable, the cells were digested with trypsin solution (0.25%) from the bottom of culture bottle. After pouring the cell dissociation buffer to the centrifugetube, nutrient solution was added to stop digestion. The centrifugetube were centrifuged for 10 min under 800 r/min, the liquid supernatant was removed, 5 mL culture solution was added, after mixing by pipetting the cell, took 10 μL cell suspension to the cell counting plat, and adjusted the cell concentration to $10^4$/well. Among the 96 wells, A1 is empty, 100 μL of cell suspension were added to the other wells. The 96 well plates were incubated in the incubator for 24 h.

(2) 50 μL dimethyl sulfoxide was used to dissolve the test samples, and then a suitable amount of culture media was added so as to reach a final concentration of 2 mg/mL. Then the samples were diluted to 20, 4, 0.8, 0.16, 0.032 mg/mL in a 24-well plate, respectively.

There were three wells for each concentration, wherein the cell growth in the surrounding two rows and columns was significantly influenced by environments and thus only taken as blank cell wells. The 96-well plates were placed in an incubator and cultivated for 72 hours.

(3) The culture media containing the compounds in the 96-well plates was discarded, and the cells were washed with phosphate buffered solution (PBS) twice. Each well was added with 100 μL MTT (tetrazole) (0.5 mg/mL), and then placed in an incubator to incubate for 4 hours, after which MTT solution was discarded and 100 μL dimethyl sulfoxide was added thereto. The reaction product of survival cells with MTT, i.e. formazan, was dissolved completely by oscillation on a magnetic oscillator, then placed into a microplate reader to measure the results, and the $IC_{50}$ values of compounds could be deduced by Bliss method.

As illustrated in Table 1, all the target compounds showed moderate to excellent antitumour activity against H460, HT-29, MKN-45, SMMC-7721, MDA-MB-231 and U87MG.

TABLE 1

| Example | H460 $IC_{50}$(μg/mL) | HT-29 $IC_{50}$(μg/mL) | MKN-45 $IC_{50}$(μg/mL) | SMMC-7721 $IC_{50}$(μg/mL) | MDA-MB-231 $IC_{50}$(μg/mL) | U87MG $IC_{50}$(μg/mL) |
|---|---|---|---|---|---|---|
| Example 1 | 0.093 | 0.18 | 0.26 | 0.29 | 0.088 | 0.17 |
| Example 2 | 0.15 | 0.17 | 0.18 | 0.43 | 0.12 | 0.31 |
| Example 3 | 0.11 | 0.42 | 0.12 | 2.1 | 0.13 | 0.33 |
| Example 4 | 0.084 | 0.093 | 0.11 | 0.23 | 0.066 | 0.25 |
| Example 5 | 0.012 | 0.0088 | 0.012 | 0.16 | 0.010 | 0.19 |
| Example 6 | 0.99 | 1.2 | 1.3 | 1.7 | 0.85 | 0.91 |
| Example 7 | 0.0012 | 0.00060 | 0.0021 | 0.13 | 0.011 | 0.10 |
| Example 8 | 1.4 | 6.1 | 3.7 | 4.9 | 0.90 | 2.7 |
| Example 9 | 0.12 | 0.20 | 0.14 | 0.50 | 0.11 | 0.42 |
| Example 10 | 0.0092 | 0.0015 | 0.038 | 0.16 | 0.011 | 0.019 |
| Example 11 | 0.17 | 0.069 | 0.13 | 0.42 | 0.15 | 0.13 |
| Example 12 | 0.33 | 0.15 | 0.62 | 1.0 | 0.40 | 0.95 |
| Example 13 | 0.097 | 0.16 | 0.27 | 0.29 | 0.16 | 0.33 |
| Example 14 | 1.2 | 0.81 | 0.65 | 1.5 | 0.90 | 1.4 |
| Example 15 | 1.5 | 0.93 | 1.1 | 2.7 | 1.1 | 3.2 |
| Example 16 | 0.019 | 0.0015 | 0.0092 | 0.10 | 0.0070 | 0.091 |
| Example 17 | 0.069 | 0.0057 | 0.072 | 0.13 | 0.071 | 0.24 |
| Example 18 | 0.19 | 0.10 | 0.13 | 0.47 | 0.21 | 0.49 |
| Example 19 | 0.96 | 1.4 | 0.71 | 0.97 | 1.2 | 1.9 |
| Example 20 | 1.1 | 0.84 | 1.5 | 6.7 | 1.7 | 4.2 |
| Example 21 | 0.16 | 0.065 | 0.10 | 0.98 | 0.087 | 0.89 |
| Example 22 | 0.29 | 0.19 | 0.37 | 1.2 | 0.31 | 0.66 |
| Example 23 | 3.6 | — | 5.7 | 5.9 | 2.9 | 5.6 |
| Example 24 | 0.14 | 0.11 | 0.23 | 1.2 | 0.21 | 0.63 |
| Example 25 | 0.0066 | 0.0013 | 0.025 | 0.095 | 0.019 | 0.12 |
| Example 26 | 5.7 | 21 | 9.8 | 13 | 4.9 | — |
| Example 27 | 1.3 | 0.59 | 0.20 | 0.53 | 0.96 | 1.4 |
| Example 28 | 0.27 | 0.18 | 0.25 | 0.95 | 0.31 | 0.88 |
| Example 29 | 0.011 | 0.0019 | 0.021 | 0.056 | 0.011 | 0.090 |
| Example 30 | 0.0012 | 0 | 0.0020 | 0.44 | 0.0021 | 0.051 |
| Example 31 | 0.041 | 0.013 | 0.11 | 0.39 | 0.059 | 0.22 |
| Example 32 | 0.19 | 0.24 | 0.33 | 0.77 | 0.13 | 1.2 |
| Example 33 | 0.19 | 0.11 | 0.23 | 0.31 | 0.12 | 0.30 |
| Example 34 | 0.089 | 0.076 | 0.12 | 0.24 | 0.077 | 0.19 |
| Example 35 | 0 | 0.045 | 0.029 | 0.17 | 0.0030 | 0.091 |
| Example 36 | 0.034 | 0.012 | 0.11 | 0.35 | 0.048 | 0.29 |
| Example 37 | 0.089 | 0.13 | 0.56 | 0.43 | 0.13 | 0.50 |

TABLE 1-continued

| Example | H460 IC$_{50}$(μg/mL) | HT-29 IC$_{50}$(μg/mL) | MKN-45 IC$_{50}$(μg/mL) | SMMC-7721 IC$_{50}$(μg/mL) | MDA-MB-231 IC$_{50}$(μg/mL) | U87MG IC$_{50}$(μg/mL) |
|---|---|---|---|---|---|---|
| Example 38 | 0.16 | 0.28 | 0.11 | 1.4 | 0.18 | 0.90 |
| Example 39 | 1.1 | 0.94 | 0.59 | 1.7 | 0.97 | 1.6 |
| Example 40 | 2.8 | 1.9 | 1.5 | 3.1 | 1.9 | — |
| Example 41 | 0.097 | 0.13 | 0.10 | 0.66 | 0.088 | 0.54 |
| Example 42 | 0.38 | 0.55 | 0.34 | 0.96 | 0.29 | 1.0 |
| Example 43 | 0.0067 | 0.0031 | 0 | 0.069 | 0.0029 | 0.092 |
| Example 44 | 0.0065 | 0.019 | 0.0007 | 0.098 | 0.0042 | 0.17 |
| Example 45 | 0.11 | 0.19 | 0.37 | 1.0 | 0.17 | 0.90 |
| Example 46 | 0.33 | 0.45 | 0.23 | 0.69 | 0.25 | 1.2 |
| Example 47 | 0.019 | 0.0078 | 0.024 | 0.099 | 0.082 | 0.11 |
| Example 48 | 0.077 | 0.16 | 0.082 | 0.20 | 0.13 | 0.33 |
| Example 49 | 0.0075 | 0.010 | 0.0039 | 0.034 | 0.00050 | 0.094 |
| Example 50 | 0.088 | 0.11 | 0.027 | 0.34 | 0.043 | 0.10 |
| Example 51 | 0.23 | 0.31 | 0.98 | 1.4 | 0.19 | 0.69 |
| Example 52 | 0.19 | 0.44 | 0.39 | 1.2 | 0.23 | 0.77 |
| Example 53 | 0.32 | 0.19 | 0.48 | 0.53 | 0.25 | 0.54 |
| Example 54 | 1.5 | 1.3 | 2.0 | 2.7 | 0.96 | 1.8 |
| Example 55 | 0.97 | 0.65 | 0.43 | 1.1 | 0.65 | 0.90 |
| Example 56 | 0.66 | 0.47 | 0.51 | 1.9 | 0.71 | 0.99 |
| Example 57 | 0.091 | 0.12 | 0.15 | 0.33 | 0.10 | 0.28 |
| Example 58 | 0.019 | 0.18 | 0.038 | 0.33 | 0.0089 | 0.21 |
| Example 59 | 0.60 | 1.4 | 0.80 | 3.5 | 0.45 | 1.9 |
| Example 60 | 0.22 | 0.11 | 0.13 | 0.73 | 0.17 | 0.88 |
| Example 61 | 0.054 | 0.076 | 0.15 | 0.22 | 0.092 | 0.21 |
| Example 62 | 0.079 | 0.11 | 0.17 | 0.16 | 0.11 | 0.76 |
| Example 63 | 0.33 | 0.50 | 0.73 | 0.64 | 0.14 | 1.0 |
| Example 64 | 0.56 | 0.34 | 0.65 | 1.0 | 0.98 | 1.7 |
| Example 65 | 2.4 | 1.9 | 4.8 | 2.8 | 2.1 | 3.4 |
| Example 66 | 1.0 | 0.58 | 0.94 | 1.5 | 0.92 | 1.7 |
| Example 67 | 1.1 | 0.90 | 1.6 | 1.1 | 0.87 | 1.4 |
| Example 68 | 1.9 | 1.7 | 2.2 | 2.1 | 1.3 | 3.0 |
| Cisplatin | 0.23 | 1.0 | 0.68 | 0.90 | 0.46 | 0.19 | c-Met Kinase Assay:

c-Met Kinase Activity was Measured with an ELISA Reader. The Specific Operation as Follows:

To the plate filled with 0.25 mg/mL PGT, the compounds, 50 pM c-Met (His-tagged recombinant human Met (Amino acids 974-ends), by baculovirus expression) and 5 μM ATP in buffer solution (25 mM MOPS, pH 7.4, 5 mM MgCl2, 0.5 raM MnCl$_2$, 100 μM sodium orthovanadate, 0.01% Triton X-100, 1 mM DTT, 1% of DMSO1% (v/v)) was added, the solution was incubated for 20 min. The reaction mixture was removed by washing with 0.2 μg/mL conjugated horseradish peroxidase (HRP) monoclonal antibody specific for phosphotyrosine (PY20) detecting phosphorylation of the substrate polymer. 1M phosphoric acid was added to terminate the color, the chromogenic substrate (TMB) was tested by spectrophotometry at 450 nm. The c-Met kinase inhibition data was illustrated in Table 2.

TABLE 2

| Example | c-Met IC$_{50}$ (μg/mL) |
|---|---|
| Example 1 | 0.017 |
| Example 2 | 0.20 |
| Example 5 | 0.030 |
| Example 6 | 0.55 |
| Example 9 | 0.15 |
| Example 10 | 0.0070 |
| Example 12 | 0.30 |
| Example 15 | 0.67 |
| Example 24 | 0.35 |
| Example 25 | 0.0071 |
| Example 28 | 0.71 |
| Example 29 | 0.020 |
| Example 30 | 0.00020 |
| Example 32 | 0.39 |
| Example 33 | 0.20 |
| Example 35 | 0.012 |
| Example 47 | 0.021 |
| Example 48 | 0.11 |
| Example 51 | 0.69 |
| Example 52 | 0.66 |
| Example 53 | 0.58 |
| Example 55 | 0.50 |
| Example 56 | 0.47 |
| Example 59 | 0.51 |

It can be clearly seen from the results of the above test, the protected compounds in formula I in this invention have good anti-tumor activity in vitro, and are better than the anticancer drug cisplatin.

Compounds of Formula I in the invention may be used alone, but usually given with a pharmaceutically acceptable carrier, which is selected according to the desired route of administration and standard pharmaceutical practice, the following preparation methods of such various pharmaceutical dosages (tablets, capsules, injections, aerosols, suppositories, films, pills, liniment, topical ointments) were used to describe new application in the pharmaceutical field.

Example 69: Tablet 10 g compound (e.g., the compound of Example 12) containing the compound of claim 1 was mixed homogeneously with 20 g adjuvants and tabletted into 100 tablets by general compression method, 300 mg each tablet.

Example 70: Capsule 10 g compound (e.g., the compound of Example 36) containing the compound of claim 1 was mixed homogeneously with 20 g adjuvants according to the requirements of pharmaceutical capsules, and filled into empty capsules, 300 mg each capsule.

Example 71: Injection 10 g compound (e.g., the compound of Example 1) containing the compound of claim 1 was absorbed by activate charcoal by conventional pharmaceutical method, filtered through 0.65 μm microporous membrane and filled into nitrogen bottle to prepare water injection preparation, 2 mL each bottle, and 100 bottles in total.

Example 72: Aerosol 10 g compound (e.g., the compound of Example 22) containing the compound of claim 1 was dissolved with a suitable amount of propylene glycol, and added with distilled water and other adjuvants to get 500 mL clear solution.

Example 73: Suppository 10 g compound (e.g., the compound of Example 19) containing the compound of claim 1 was grinded and a suitable amount of glycerol was added and mixed homogeneously. Then melt glycerol gelatin was added and grinded homogeneously, and the mixture was poured into a mold coated with lubricant to produce 50 suppository particles.

Example 74: Film 10 g compound (e.g., the compound of Example 13) containing the compound of claim 1 was mixed and expanded with polyvinyl alcohol, pharmaceutically acceptable glycerol, water etc., and dissolved by heating. After filtration on an 80 mesh screen, the compound of Example 18 was added to the filtrate and dissolved therein by agitation. 100 films were produced by coater machine.

Example 75: Dripping Pill 10 g compound (e.g., the compound of Example 17) containing the compound of claim 1 was mixed homogeneously with 50 g substrate such as gelatin by heating and melting, then the mixture was dropped into a liquid paraffin at low temperature. 1000 pills of dripping pill were produced.

Example 76: Liniment for External Use 10 g compound (e.g., the compound of Example 31) containing the compound of claim 1 was mixed and ground with 2.5 g adjuvants such as emulsifier by conventional formulation methods, then 200 mL water was added to prepare the liniment for external use.

Example 77: Ointment 10 g compound (e.g., the compound of Example 47) containing the compound of claim 1 was ground and then mixed homogeneously with 500 g oleaginous base such as Vaseline.

Although the present invention has been described through specific embodiments, but modifications and equivalent changes to those skilled person in this field are apparent, and they are included within the scope of the invention.

The invention claimed is:

1. Compounds of formula I, or their pharmaceutically acceptable salts, or hydrates

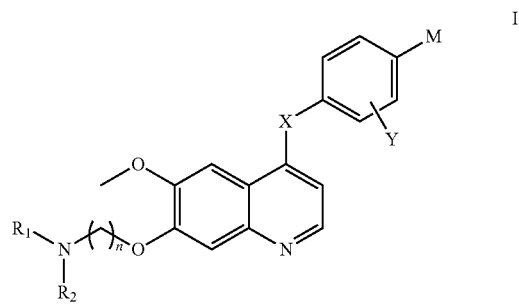

wherein,
X is O, S, NH or NCH$_3$;
Y can be 1-4 substituents independently selected from the group consisting of halogen, trihalomethyl, methyl, cyano and nitro groups;
M is

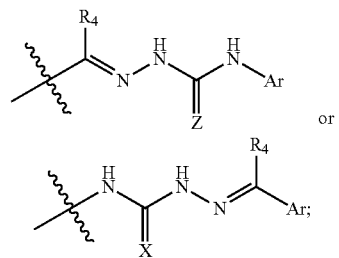

Z is O or S;
n is an integer between 1 and 6;
R$_1$ and R$_2$, which are same or different, are independently selected from hydrogen, (C$_1$-C$_{10}$) alkyl, (C$_3$-C$_7$) cycloalkyl, (C$_2$-C$_{10}$) alkenyl and (C$_2$-C$_{10}$) alkynyl, wherein R$_1$ and R$_2$ are optionally substituted with 1-3 same or different R$_3$; or
R$_1$ and R$_2$ together with the nitrogen atom to which they are attached form 5- to 10-membered heterocyclic radical or 5- to 10-membered heteroaryl radical, wherein, besides the nitrogen atom to which R$_1$ and R$_2$ are attached, the said heterocyclic and heteroaryl radicals optionally contains 1 to 4 heteroatoms selected from N, O and S, and wherein the said heterocyclic radical optionally contains 1 to 2 carbon-carbon double bonds or triple bonds, and wherein said heterocyclic and heteroaryl radicals can be optionally substituted with 1 to 3 same or different R$_3$;
R$_3$ and R$_4$ are independently hydrogen or (C$_1$-C$_6$) alkyl;
Ar is (C$_6$-C$_{10}$) aryl or 5- to 10-membered heteroaryl radical, wherein said heteroaryl radical optionally contains 1 to 3 heteroatoms selected from N, O and S, and Ar is optionally substituted with 1 to 3 same or different R$_5$; and R₅ is hydroxyl, halogen, nitro, amino, cyano, (C₁-C₆) alkyl, (C₂-C₆) alkenyl, (C₂-C₆) alkynyl, or (C₁-C₆) alkoxyl, wherein each of (C₁-C₆) alkyl, (C₂-C₆) alkenyl, (C₂-C₆) alkynyl, or (C₁-C₆) alkoxyl is optionally substituted with a substituent selected from the group consisting of hydroxyl, amino, halogen, amino group substituted with 1 or 2 (C₁-C₆) alkyl groups, (C₁-C₆) alkylcarbonylamino, carboxyl group which can be free acids, salts, amidated or form ester group, (C₁-C₆) alkylsulfinyl, (C₁-C₆) alkylsulfonyl, (C₁-C₆) alkylacyl, carbamoyl, carbamoyl substituted with 1 for 2 (C₁-C₆) alkyl, (C₁-C₃) alkylenedioxo, and allyl.

2. The compounds of the formula I, or their pharmaceutically acceptable salts, or hydrates according to claim 1, wherein,
Y can be 1-2 substituents independently selected from the group consisting of halogen, trihalomethyl, methyl, cyano and nitro groups;
n is an integer between 1 and 4; and
R₁ and R₂, which are same or different, are independently selected from hydrogen, (C₁-C₆) alkyl, (C₃-C₅) cycloalkyl, (C₂-C₆) alkenyl and (C₂-C₆) alkynyl, wherein R₁ and R₂ are optionally substituted with 1-3 same or different R₃; or
R₁ and R₂ together with the nitrogen atom to which they are attached form 5- to 10-membered heterocyclic radical, wherein besides the nitrogen atom to which R₁ and R₂ are attached, the said heterocyclic radical optionally contains 1 to 4 heteroatoms selected from N, O and S, and wherein said heterocyclic radical optionally contains 1 to 2 carbon-carbon double bonds or triple bonds, said heterocyclic radicals can be optionally substituted with 1 to 3 same or different R₃.

3. The compounds of claim 2, or their pharmaceutically acceptable salts, or hydrates, having Formula II,

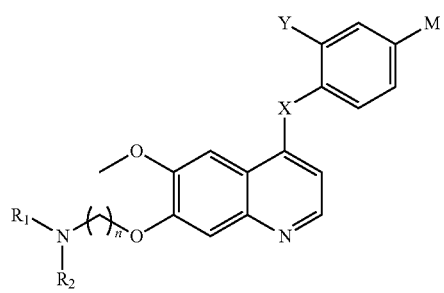

wherein,
X is O or S; and
Y is halogen, trihalomethyl, methyl, cyano or nitro groups.

4. The compounds of claim 3, or their pharmaceutically acceptable salts, or hydrates, wherein,
X is O;
n is 3 or 4;
R₁ and R₂, which are same or different, are independently selected from hydrogen, (C₁-C₄) alkyl, (C₃-C₅) cycloalkyl; or
R₁ and R₂ together with the nitrogen atom to which they are attached form 5- or 6-membered heterocyclic radical, wherein besides the nitrogen atom to which R₁ and R₂ are attached, said heterocyclic radicals optionally contains 1 or 2 heteroatoms selected from N, O and S, and wherein said heterocyclic radical optionally contains 1 or 2 carbon-carbon double bonds or triple bonds, and said heterocyclic radical can be optionally substituted with 1 to 3 same or different R₃;
R₃ is (C₁-C₄) alkyl; and
R₄ is hydrogen, methyl or ethyl.

5. The compounds of claim 4, and or pharmaceutically acceptable salts, or hydrates, wherein,
Y is F;
n is 3;
R₁ and R₂ together with the nitrogen atom to which they are attached form dimethylamino, diethylamino, piperidin-1-yl, morpholin-4-yl, 4-methylpiperazin-1-yl, piperazin1-yl, 4-methylpiperidin-1-yl, pyrrolidin-1-yl, thiomorpholin-4-yl; and
R₄ is hydrogen, methyl or ethyl.

6. The compounds of claim 5, or their pharmaceutically acceptable salts or hydrates wherein
M is

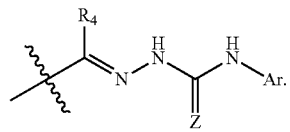

7. The compounds of claim 5, or their pharmaceutically acceptable salts, or hydrates, wherein,
M is

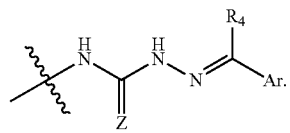

8. The compounds of claim 5, or their pharmaceutically acceptable salts, or hydrates, wherein,
Ar is phenyl, naphthyl, quinolyl, isoquinolyl, quinazolinyl, indolyl, pyridyl, furanyl, thienyl, pyrrolyl or pyrimidinyl, wherein Ar can be is optionally substituted with 1 to 3 same or different R₅.

9. The compounds of claim 8, or their pharmaceutically acceptable salts, or hydrates, wherein,
Ar is phenyl and Ar can be optionally substituted with 1 to 3 same or different R₅; and
R₅ is halogen, hydroxyl, nitro, cyano, trifluoromethyl, trifluoromethoxy, (C₁-C₄) alkyl, (C₁-C₄) alkoxy, allyl, dimethylamino.

10. The compounds of claim 9, or their pharmaceutically acceptable salts, or hydrates, wherein,
R₁ and R₂ together with the nitrogen atom to which they are attached form piperidin-1-yl, morpholin-4-yl, 4-methylpiperazin-1-yl, 4-methylpiperidin-1-yl, or pyrrolidin-1-yl; and
R₄ is H.

11. The compounds of the formula I of claim 1, or their pharmaceutically acceptable salts, or hydrates, the compounds being:
(E)-N¹-(3-fluoro-4-(6-methoxy-7-(3-(pyrrolidin-1-yl) propoxy)quinoline-4-yloxy)phenyl)-N⁴-(benzaldehyde)semicarbazone;
(E)-N¹-(3-fluoro-4-(6-methoxy-7-(3-(4-methylpiperidin-1-yl)propoxy)quinoline-4-yloxy)phenyl)-N⁴-(benzaldehyde)semicarbazone;

(E)-N¹-(3-fluoro-4-(6-methoxy-7-(3-(morpholin-4-yl)
   propoxy)quinoline-4-yloxy)phenyl)-N⁴-(benzalde-
   hyde)semicarbazone;
(E)-N¹-(3-fluoro-4-(6-methoxy-7-(3-(4-methylpiperazin-
   1-yl)propoxy)quinoline-4-lyoxy)phenyl)-N⁴-(benzal-
   dehyde)semicarbazone;
(E)-N¹-(3-fluoro-4-(6-methoxy-7-(3-(piperidin-1-yl)
   propoxy)quinoline-4-yloxy)phenyl)-N⁴-(benzalde-
   hyde)semicarbazone;
(E)-N¹-(3-fluoro-4-(6-methoxy-7-(3-(pyrrolidin-1-yl)
   propoxy)quinoline-4-yloxy)phenyl)-N⁴-(3-methoxy-
   benzaldehyde)semicarbazone;
(E)-N¹-(3-fluoro-4-(6-methoxy-7-(3-(4-methylpiperidin-
   1-yl)propoxy)quinoline-4-yloxy)-phenyl)-N⁴-(3-
   methoxybenzaldehyde)semicarbazone;
(E)-N¹-(3-fluoro-4-(6-methoxy-7-(3-(morpholin-4-yl)
   propoxy)quinoline-4-yloxy)phenyl)-N⁴-(3-methoxy-
   benzaldehyde)semicarbazone;
(E)-N¹-(3-fluoro-4-(6-methoxy-7-(3-(piperidin-1-yl)
   propoxy)quinoline-4-yloxy)phenyl)-N⁴-(3-methoxy
   benzaldehyde)semicarbazone;
(E)-N¹-(3-fluoro-4-(6-methoxy-7-(3-(4-methylpiperidin-
   1-yl)propoxy)quinoline-4-lyoxy)phenyl)-N⁴-(4-fluo-
   robenzaldehyde)semicarbazone;
(E)-N¹-(3-fluoro-4-(6-methoxy-7-(3-(piperidin-1-yl)
   propoxy)quinoline-4-yloxy)phenyl)-N⁴-(4-fluorobenz-
   aldehyde)semicarbazone;
(E)-N¹-(3-fluoro-4-(6-methoxy-7-(3-(pyrrolidin-1-yl)
   propoxy)quinoline-4-yloxy)phenyl)-N⁴-(2-chloro-4-
   fluorobenzaldehyde)semicarbazone;
(E)-N¹-(3-fluoro-4-(6-methoxy-7-(3-(4-methylpiperidin-
   1-yl)propoxy)quinoline-4-yloxy)phenyl)-N⁴-(2-
   chloro-4-fluorobenzaldehyde)semicarbazone;
(E)-N¹-(3-fluoro-4-(6-methoxy-7-(3-(morpholin-4-yl)
   propoxy)quinoline-4-yloxy)phenyl)-N⁴-(2-chloro-4-
   fluorobenzaldehyde)semicarbazone;
(E)-N¹-(3-fluoro-4-(6-methoxy-7-(3-(pyrrolidin-1-yl)
   propoxy)quinoline-4-yloxy)phenyl)-N⁴-(2-nitrobenz-
   aldehyde)semicarbazone;
(E)-N¹-(3-fluoro-4-(6-methoxy-7-(3-(4-methylpiperidin-
   1-yl)propoxy)quinoline-4-yloxy)phenyl)-N⁴-(2-ni-
   trobenzaldehyde)semicarbazone;
(E)-N¹-(3-fluoro-4-(6-methoxy-7-(3-(piperidin-1-yl)
   propoxy)quinoline-4-yloxy)phenyl)-N⁴-(2-nitrobenz-
   aldehyde)semicarbazone;
(E)-N¹-(3-fluoro-4-(6-methoxy-7-(3-(pyrrolidin-1-yl)
   propoxy)quinoline-4-yloxy)phenyl)-N⁴-(2-hydroxyl-1-
   naphthaldehyde)semicarbazone;
(E)-N¹-(3-fluoro-4-(6-methoxy-7-(3-(pyrrolidin-1-yl)
   propoxy)quinoline-4-yloxy)phenyl)-N⁴-(2,4-dichlo-
   robenzaldehyde) semicarbazone;
(E)-N¹-(3-fluoro-4-(6-methoxy-7-(3-(morpholin-4-yl)
   propoxy)quinoline-4-yloxy)phenyl)-N⁴-(2,4-dichlo-
   robenzaldehyde)semicarbazone;
(E)-N¹-(3-fluoro-4-(6-methoxy-7-(3-(4-methylpiperidin-
   1-yl)propoxy)quinoline-4-yloxy)phenyl)-N⁴-(2-hy-
   droxy-1-naphthaldehyde)semicarbazone;
(E)-N¹-(3-fluoro-4-(6-methoxy-7-(3-(pyrrolidin-1-yl)
   propoxy)quinoline-4-lyoxy)phenyl)-N⁴-(3,4-difluo-
   robenzaldehyde)semicarbazone;
(E)-N¹-(3-fluoro-4-(6-methoxy-7-(3-(morpholin-4-yl)
   propoxy)quinoline-4-oxy)phenyl)-N⁴-(3,4-difluo-
   robenzaldehyde)semicarbazone;
(E)-N¹-(3-fluoro-4-(6-methoxy-7-(3-(pyrrolidin-1-yl)
   propoxy)quinoline-4-yloxy)phenyl)-N⁴-(3-trifluorom-
   ethylbenzaldehyde)semicarbazone;
(E)-N¹-(3-fluoro-4-(6-methoxy-7-(3-(4-methylpiperidin-
   1-yl)propoxy)quinoline-4-yloxy)phenyl)-N⁴-(2, 4-dif-
   luorobenzaldehyde)semicarbazone;
(E)-N¹-(3-fluoro-4-(6-methoxy-7-(3-(morpholin-4-yl)
   propoxy)quinoline-4-yloxy)phenyl)-N⁴-(3-trifluorom-
   ethylbenzaldehyde)semicarbazone;
(E)-N¹-(3-fluoro-4-(6-methoxy-7-(3-(morpholin-4-yl)
   propoxy)quinoline-4-yloxy)phenyl)-N⁴-(3,5-dimethyl-
   4-hydroxybenzaldehyde)semicarbazone;
(E)-N¹-(3-fluoro-4-(6-methoxy-7-(3-(morpholin-4-yl)
   propoxy)quinoline-4-yloxy)phenyl)-N⁴-(2-hydroxyl-1-
   naphthaldehyde)semicarbazone;
(E)-N¹-(3-fluoro-4-(6-methoxy-7-(3-(pyrrolidin-1-yl)
   propoxy)quinoline-4-yloxy)phenyl)-N⁴-(3-allyl-2-hy-
   droxybenzaldehyde)semicarbazone;
(E)-N¹-(3-fluoro-4-(6-methoxy-7-(3-(pyrrolidin-1-yl)
   propoxy)quinoline-4-yloxy)phenyl)-N⁴-(3-allyl-2-hy-
   droxybenzaldehyde)semicarbazone;
(E)-N¹-(3-fluoro-4-(6-methoxy-7-(3-(piperidin-1-yl)
   propoxy)quinoline-4-yloxy)phenyl)-N⁴-(3,4-difluo-
   robenzaldehyde)thiosemicarbazone;
(E)-N¹-(3-fluoro-4-(6-methoxy-7-(3-(pyrrolidin-1-yl)
   propoxy)quinoline-4-yloxy)phenyl])-N⁴-(2-nitrobenz-
   aldehyde)thiosemicarbazone;
(E)-N¹-(3-fluoro-4-(6-methoxy-7-(3-(morpholin-4-yl)
   propoxy)quinoline-4-yloxy)phenyl)-N⁴-(2-nitrobenz-
   aldehyde)thiosemicarbazone;
(E)-N¹-(3-fluoro-4-(6-methoxy-7-(3-(piperidin-1-yl)
   propoxy)quinoline-4-yloxy)phenyl)-N⁴-(2-nitrobenz-
   aldehyde)thiosemicarbazone;
(E)-N¹-(3-fluoro-4-(6-methoxy-7-(3-(morpholin-4-yl)
   propoxy)quinoline-4-yloxy)phenyl)-N⁴-(3-allyl-2-hy-
   droxybenzaldehyde)thiosemicarbazone;
(E)-N¹-(3-fluoro-4-(6-methoxy-7-(3-(pyrrolidin-1-yl)
   propoxy)quinoline-4-yloxy)phenyl)-N⁴-(benzalde-
   hyde)thiosemicarbazone;
(E)-N¹-(3-fluoro-4-(6-methoxy-7-(3-(4-methylpiperidin-
   1-yl)propoxy)quinoline-4-yloxy)phenyl)-N⁴-(benzal-
   dehyde)thiosemicarbazone;
(E)-N¹-(3-fluoro-4-(6-methoxy-7-(3-(morpholin-4-yl)
   propoxy)quinoline-4-yloxy)phenyl)-N⁴-(benzalde-
   hyde)thiosemicarbazone;
(E)-N¹-(3-fluoro-4-(6-methoxy-7-(3-(4-methyl-1-piper-
   azinyl)propoxy)quinoline-4-yloxy)phenyl)-N⁴-(benz-
   aldehyde)thiosemicarbazone;
(E)-N¹-(3-fluoro-4-(6-methoxy-7-(3-(4-methyl-1-piper-
   azinyl)propoxy)quinoline-4-yloxy)phenyl)-N⁴-(2,4-di-
   chlorobenzaldehyde)thiosemicarbazone;
(E)-N¹-(3-fluoro-4-(6-methoxy-7-(3-(piperidin-1-yl)
   propoxy)quinoline-4-yloxy)phenyl)-N⁴-(2,4-dichlo-
   robenzaldehyde)thiosemicarbazone;
(E)-N¹-(3-fluoro-4-(6-methoxy-7-(3-(4-methyl-1-piper-
   azinyl)propoxy)quinoline-4-yloxy)phenyl)-N⁴-(2-
   chloro-4-fluorobenzaldehyde)thiosemicarbazone;
(E)-N¹-(3-fluoro-4-(6-methoxy-7-(3-(piperidin-1-yl)
   propoxy)quinoline-4-yloxy)phenyl)-N⁴-(2-chloro-4-
   fluorobenzaldehyde)thiosemicarbazone;
(E)-N¹-(3-fluoro-4-(6-methoxy-7-(3-(pyrrolidin-1-yl)
   propoxy)quinoline-4-yloxy)phenyl)-N⁴-(4-fluorobenz-
   aldehyde)thiosemicarbazone; or
(E)-N¹-(3-fluoro-4-(6-methoxy-7-(3-(morpholin-4-yl)
   propoxy)quinoline-4-yloxy)phenyl)-N⁴-(4-fluorobenz-
   aldehyde)thiosemicarbazone.

12. The compounds of the formula I of claim 1, or their pharmaceutically acceptable salts, or hydrates, the compounds being:

(E)-N$^1$-(4-chloro-3-(trifluoromethyl)phenyl)-N$^4$-(3-fluoro-4-(6-methoxy-7-(3-(piperidin-1-yl)propoxy)quinoline-4-yloxy)benzaldehyde)semicarbazone;

(E)-N$^1$-(2-fluorophenyl)-N$^4$-(3-fluoro-4-(6-methoxy-7-(3-(piperidin-1-yl)propoxy) quinoline-4-yloxy)benzaldehyde)semicarbazone;

(E)-N$^1$-(3,5-dichlorophenyl)-N$^4$-(3-fluoro-4-(6-methoxy-7-(3-(piperidin-1-yl)propoxy) quinoline-4-yloxy)benzaldehyde)semicarbazone;

(E)-N$^1$-(3,5-dimethoxyphenyl)-N$^4$-(3-fluoro-4-(6-methoxy-7-(3-(piperidin-1-yl)propoxy) quinoline-4-yloxy)benzaldehyde)semicarbazone;

(E)-N$^1$-(3-fluoro-6-methylphenyl)-N$^4$-(-3-fluoro-4-(6-methoxy-7-(3-(piperidin-1-yl)propoxy) quinoline-4-yloxy)benzaldehyde)semicarbazone;

(E)-N$^1$-(4-chloro-3-(trifluoromethyl)phenyl)-N$^4$-(3-fluoro-4-(6-methoxy-7-(3-(4-methyl-1-piperazinyl)propoxy)quinoline-4-yloxy)benzaldehyde)semicarbazone;

(E)-N$^1$-phenyl-N$^4$-(3-fluoro-4-(6-methoxy-7-(3-(4-methyl-1-piperazinyl)propoxy) quinoline-4-yloxy)benzaldehyde)semicarbazone;

(E)-N$^1$-(4-chlorophenyl)-N$^4$-(3-fluoro-4-(6-methoxy-7-(3-(4-methyl-1-piperazinyl)propoxy)-quinoline-4-yloxy)benzaldehyde)semicarbazone;

(E)-N$^1$-(3-bromophenyl)-N$^4$-(3-fluoro-4-(6-methoxy-7-(3-(morpholin-4-yl)propoxy)quinoline-4-yloxy)benzaldehyde)semicarbazone;

(E)-N$^1$-phenyl-N$^4$-(3-fluoro-4-(6-methoxy-7-(3-(morpholin-4-yl)propoxy)quinoline-4-yloxy)benzaldehyde)semicarbazone;

(E)-N$^1$-(3,5-difluorophenyl)-N$^4$-(3-fluoro-4-(6-methoxy-7-(3-(morpholin-4-yl)propoxy) quinoline-4-yloxy)benzaldehyde)semicarbazone;

(E)-N$^1$-(3,5-dimethoxyphenyl)-N$^4$-(3-fluoro-4-(6-methoxy-7-(3-(morpholin-4-yl)propoxy) quinoline-4-oxy)benzaldehyde)semicarbazone;

(E)-N$^1$-phenyl-N$^4$-(3-fluoro-4-(6-methoxy-7-(3-(4-methylpiperidin-1-yl)propoxy) quinoline-4-yloxy)benzaldehyde)semicarbazone;

(E)-N$^1$-(3,5-dimethoxyphenyl)-N$^4$-(3-fluoro-4-(6-methoxy-7-(3-(4-methylpiperidin-1-yl)propoxy)quinoline-4-yloxy)benzaldehyde)semicarbazone;

(E)-N$^1$-(2-fluorophenyl)-N$^4$-(3-fluoro-4-(6-methoxy-7-(3-(4-methylpiperidin-1-yl)propoxy)quinoline-4-yloxy)benzaldehyde)semicarbazone;

(E)-N$^1$-(3,5-dichlorophenyl)-N$^4$-(3-fluoro-4-(6-methoxy-7-(3-(piperidin-1-yl)propoxy)quinoline-4-yloxy)benzaldehyde)thiosemicarbazone;

(E)-N$^1$-(3,5-dimethoxyphenyl)-N$^4$-(4-(6-methoxy-7-(3-(piperidin-1-yl)propoxy)quinoline-4-yloxy)-3-fluorobenzaldehyde)thiosemicarbazone;

(E)-N$^1$-phenyl-N$^4$-(3-fluoro-4-(6-methoxy-7-(3-(4-methylpiperidin-1-yl)propoxy) quinoline-4-yloxy)benzaldehyde)thiosemicarbazone;

(E)-N$^1$-[4-chloro-3-(trifluoromethyl)phenyl]-N$^4$-(3-fluoro-4-(6-methoxy-7-(3-(4-methylpiperidin-1-yl)propoxy)quinoline-4-yloxy)benzaldehyde)thiosemicarbazone;

(E)-N$^1$-(3-bromophenyl)-N$^4$-(3-fluoro-4-(6-methoxy-7-(3-(morpholin-4-yl)propoxy)quinoline-4-yloxy)benzaldehyde)thiosemicarbazone;

(E)-N$^1$-(3,5-difluorophenyl)-N$^4$-(3-fluoro-4-(6-methoxy-7-(3-(morpholin-4-yl)propoxy)quinoline-4-yloxy)benzaldehyde)thiosemicarbazone;

(E)-N$^1$-phenyl-N$^4$-(3-fluoro-4-(6-methoxy-7-(3-(4-methyl-1-piperazinyl)propoxy)quinoline-4-yloxy)benzaldehyde)thiosemicarbazone; or (E)-N$^1$-(4-chlorophenyl)-N$^4$-(3-fluoro-4-(6-methoxy-7-(3-(4-methyl-1-piperazinyl)propoxy)quinoline-4-yloxy)benzaldehyde)thiosemicarbazone.

13. A pharmaceutical composition, comprising the compounds or pharmaceutically acceptable salts or hydrates thereof according to claim 1 as active ingredient and a pharmaceutically acceptable excipient.

14. A method for treating a cancer, the method comprising administering, to a patient in need thereof, a therapeutically effective amount of a compound of claim 1, or a pharmaceutically acceptable salt, or hydrate, wherein the cancer is lung cancer liver cancer, stomach cancer, colon cancer, breast cancer, malignant glioblastoma.

\* \* \* \* \*

UNITED STATES PATENT AND TRADEMARK OFFICE
CERTIFICATE OF CORRECTION

PATENT NO. : 9,783,499 B2
APPLICATION NO. : 14/703769
DATED : October 10, 2017
INVENTOR(S) : Ping Gong et al.

Page 1 of 1

It is certified that error appears in the above-identified patent and that said Letters Patent is hereby corrected as shown below:

In the Claims

Column 52, Lines 37-43:

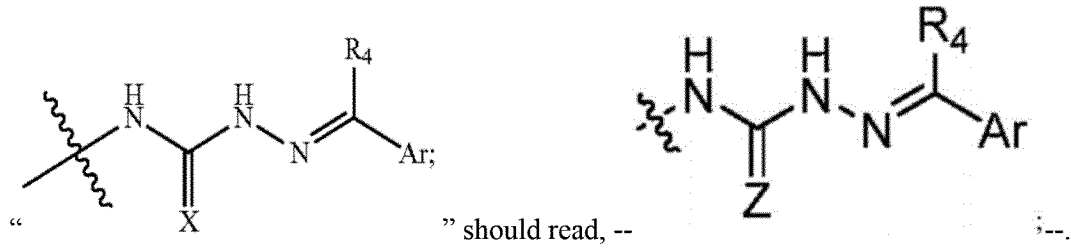

Column 54, Line 17:
"acceptable salts or hydrates wherein" should read, --acceptable salts, or hydrates, wherein,--.

Column 54, Line 43:
"pyrimidinyl, wherein Ar can be is optionally substituted" should read, --pyrimidinyl, wherein Ar is optionally substituted--.

Signed and Sealed this
Twenty-eighth Day of August, 2018

Andrei Iancu
*Director of the United States Patent and Trademark Office*